(12) United States Patent
Khan et al.

(10) Patent No.: US 11,981,695 B2
(45) Date of Patent: May 14, 2024

(54) LINOLEIC ACID DERIVATIVES, PHARMACEUTICAL COMPOSITION OR FOOD COMPOSITION COMPRISING SAID LINOLEIC ACID DERIVATIVES, AND THEIR USES

(71) Applicants: UNIVERSITÉ DE BOURGOGNE, Dijon (FR); INSERM (INSTITUT NATIONAL DE LA SANTÉ ET DE LA RECHERCHE MÉDICALE), Paris (FR)

(72) Inventors: Naim Khan, Quetigny (FR); Sylvain Juge, Dijon (FR); Aziz Hichami, Is sur Tille (FR); Jérôme Bayardon, Dijon (FR); Marie-Laure Louillat-Habermeyer, Dijon (FR); Baptiste Rugeri, Gif sur Yvette (FR)

(73) Assignees: UNIVERSITÉ DE BOURGOGNE, Dijon (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 839 days.

(21) Appl. No.: 17/059,361
(22) PCT Filed: May 27, 2019
(86) PCT No.: PCT/EP2019/063696
§ 371 (c)(1),
(2) Date: Nov. 27, 2020
(87) PCT Pub. No.: WO2019/229005
PCT Pub. Date: Dec. 5, 2019

(65) Prior Publication Data
US 2021/0155640 A1 May 27, 2021

(30) Foreign Application Priority Data
May 28, 2018 (EP) .................... 18305648

(51) Int. Cl.
A23K 20/158 (2016.01)
A23L 33/00 (2016.01)
(Continued)

(52) U.S. Cl.
CPC .......... C07F 9/4015 (2013.01); A23K 20/158 (2016.05); A23L 33/12 (2016.08);
(Continued)

(58) Field of Classification Search
CPC ......... A23K 20/158; A23K 20/40; A61P 3/04; C07D 233/47; C07D 263/16;
(Continued)

(56) References Cited

U.S. PATENT DOCUMENTS

2015/0050408 A1* 2/2015 Shi .......... A23L 27/60
426/534

FOREIGN PATENT DOCUMENTS

WO 2013/149031 10/2013

OTHER PUBLICATIONS

José Antonio Cisneros, et al., "Structure-Activity Relationship of a Series of Inhibitors of Monoacylglycerol Hydrolysis-Comparison with Effects upon Fatty Acid Amide Hydrolase", Journal of Medicinal Chemistry, vol. 50, No. 20, Oct. 1, 2007, pp. 5012-5023 (12 pages).

(Continued)

Primary Examiner — Timothy R Rozof
(74) Attorney, Agent, or Firm — NIXON & VANDERHYE

(57) ABSTRACT

Disclosed is a linoleic acid derivative of Formula (I) below including a hydrophobic part $C_{17}H_{31}$ linked to a polar head part "A":

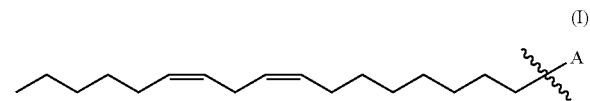

(I)

wherein the polar head part A is selected from $A^1$ to $A^4$ below:

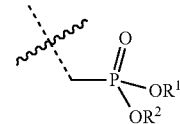

A1

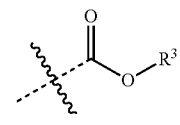

A2

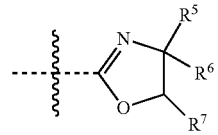

A3

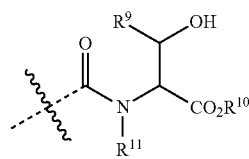

A4 or a pharmaceutically/food quality acceptable salt thereof.

19 Claims, 12 Drawing Sheets

(51) Int. Cl.
  A23L 33/12    (2016.01)
  A61P 3/04     (2006.01)
  C07C 233/47   (2006.01)
  C07D 263/16   (2006.01)
  C07D 303/16   (2006.01)
  C07D 305/06   (2006.01)
  C07D 307/12   (2006.01)
  C07D 319/06   (2006.01)
  C07F 9/40     (2006.01)

(52) U.S. Cl.
  CPC ............... *A23L 33/40* (2016.08); *A61P 3/04* (2018.01); *C07C 233/47* (2013.01); *C07D 263/16* (2013.01); *C07D 303/16* (2013.01); *C07D 305/06* (2013.01); *C07D 307/12* (2013.01); *C07D 319/06* (2013.01); *A23V 2002/00* (2013.01)

(58) Field of Classification Search
  CPC .. C07D 303/16; C07D 305/06; C07D 307/12; C07D 319/06
  See application file for complete search history.

(56) References Cited

OTHER PUBLICATIONS

N. Godinot, et al., "Activation of Tongue-Expressed GPR40 and GPR120 By Non Caloric Agonists is Not Sufficient to Drive Preference in Mice", Neuroscience, vol. 250, 2013, pp. 20-30 (11 pages).

Sonyuan Lin, et al., "Novel Analogues f Arachidonylethanolamide (Anadamide): Affinities for the CB1 and CB2 Cannabinoid Receptors and Metabolic Stability", Journal of Medicinal Chemistry, vol. 41, No. 27, Dec. 1, 1998, pp. 5353-5361 (9 pages).

International Search Report for PCT/EP2019/063696 dated Aug. 7, 2019, 4 pages.

Written Opinion of the ISA for PCT/EP2019/063696 dated Aug. 7, 2019, 5 pages.

* cited by examiner

NKS-5

NKS-3

NKS-3

NKS-5

NKS-5

NKS-3

NKS-3

LINOLEIC ACID DERIVATIVES, PHARMACEUTICAL COMPOSITION OR FOOD COMPOSITION COMPRISING SAID LINOLEIC ACID DERIVATIVES, AND THEIR USES

This application is the U.S. national phase of International Application No. PCT/EP2019/063696 filed May 27, 2019 which designated the U.S. and claims priority to EP Patent Application No. 18305648.0 filed May 28, 2018, the entire contents of each of which are hereby incorporated by reference.

FIELD OF THE INVENTION

The present invention relates to field of products dedicated to the therapeutic treatment or cosmetic treatment of weight-related disorders such as excess weight or obesity, linked to excessive intake of dietary fatty acids.

Especially, the present invention refers to compounds that are able to bind to or to modulate the activity of lingual taste receptors, such as CD36 and/or GPR120 that are involved in the detection and orosensory perception of these fatty acids. In particular, the compounds of the invention are derived from a natural fatty acid, which is linoleic fatty acid.

The present invention also refers to the use of these compounds for the cosmetic or the therapeutic treatment linked to weight-related disorders.

DESCRIPTION OF RELATED ART

Defined as a medical condition in which excess body fat has accumulated to the extent that it may have a negative impact on health, obesity is one of the main priorities of the World Health Organization (WHO report no 311, 2016), as regards disease prevalence and management. Indeed, on a world scale, 600 million people are obese, thus representing about 15 to 30% of the population in industrialized countries. It is also estimated that 43 million kids under the age of five are overweight and thus have a higher risk of developing obesity once they become adult. Moreover, the increasing prevalence of obesity in the global population goes along with an increased proportion of excess weight mothers or obese women at the start of their pregnancies. Yet, obese mothers are much more likely to give birth to obese children (called macrosomic children), especially if they suffer from gestational diabetes or from metabolic syndrome in pregnancy. In France, excess weight and obesity together affect more than 46% of adults and 19% of children (OBEpi, 2012 Report).

In general, the main risk factor which especially contributes to increase the energy balance and to produce excess weight or even obesity or to increase the fat mass is a high-energy density diet delivering a low satiety feeling, resulting from a high proportion of energy originating from fats (vegetable oils and animal fats) (i.e., hyperlipidic diet). This high-energy density diet has become a part of our way of life and eating behavior which have been fundamentally changed in the 20$^{th}$ century.

At present, dietary fat intake is almost 40% of the population in Western countries. This excessive consumption of lipids favors the incidence of plethora diseases, such as obesity mentioned above, but also type 2 diabetes, etc., with important medico-economic consequences.

Adapted dietetic and hygienic measures, combining a balanced diet and a regular physical activity, do represent the simplest way to fight against excess fat ingestion or excess weight. Yet practicing a regular physical activity is constraining and, moreover, the benefits of a restrictive diet are often limited by a weight rebound effect when starting normal eating and drinking again.

Therefore, it is important to develop compounds to prevent and treat weight disorders.

During the course of last couple of years, several strategies have been developed by industries/scientists to decrease fat contents in the diet.

Two main classes of compounds/solutions, namely "fat substitutes" or "fat mimetics" have been developed to achieve this goal. These "fat substitute" or "fat mimetics" contain saturated fat and protein- or carbohydrate-derived substances. However, these compounds are lesser palatable than natural fat and they are not, strikingly, devoid of calories, though they bring lesser calories than natural fat.

The recent discovery of fat taste as the sixth taste modality opens the door for the synthesis of a new class of molecules as taste modulators. Indeed, the sense of taste plays a key role in guiding the decision to ingest calorie rich nutritive food.

In fact, during food intake, the sapid molecules, dissolved in the saliva, activate lingual taste receptors situated at the apical pole of the taste bud cells, localized at the level of the papillae which are distributed in the lingual epithelium. A taste bud is a cluster of cells that comprises of a taste pore and four cell types with distinct functions. Type I cells (supporting cells) respond to salty substances, type II (receptor) cells respond to sweet, bitter and umami substances, type Ill (presynaptic) cells communicate via a synapse with the nerves, and the type IV cells (basal cells) are differentiated into types 1, 11 and Ill cells. There are also progenitor cells, localized around taste buds, multiply and migrate inside the papilla. All the differentiated taste cells are subjected to a continuous renewal with a half-life of about 10 days.

The taste receptors (TR), present on the taste bud cells, are chemical motifs (homo- or heterodimeric), inserted into the plasma membrane of these lingual cells. T2R receptors would be involved in the perception of bitter or toxic flavors (Nelson G et al. "Mammalian sweet taste receptors", *Cell*. 2001, Aug. 10, 106(3), 381-90). The T1R2/T1R3 heterodimer detects sweet flavors (Montmayeur J P Liberles S D et al. "candidate taste receptor gene near a sweet taste locus", *Nat. Neurosci*. 2001, May, 4(5):492-8), while the T1R1/T1R3 heterodimer is sensitive to umami (Chaudhari N et al., "A metabotropic glutamate receptor variant functions as a taste receptor", *Nat Neurosci*. 2000 February; 3(2):113-9).

The detection of dietary lipids along the oro-intestinal tract could take place through lipid-specific sensors. Lipid-specific binding proteins, expressed in the oral cavity and intestine, might perform this role. In accordance with this hypothesis, the recent data shows that the CD36 receptor, expressed on lingual papillae, plays a role in the oro-sensory perception of dietary lipids (El-Yassimi A et al. "Linoleic acid induces calcium signaling, Src kinase phosphorylation, and neurotransmitter release in mouse CD36-positive gustatory cells", *J. Biol. Chem*. 2008, May 283(19), 12949-59 and Dramane G et al. "STIM1 regulates calcium signaling in taste bud cells and preference for fat in mice", *J. Clin. Invest*. 2012, June, 122(6), 2267-82).

In addition, GPR120, a member of the G-protein coupled receptors (GPCR) family, has been identified in taste bud cells in mouse and human beings (Ozdener M H et al. "CD36- and GPR120-mediated $Ca^{2+}$ signaling in human taste bud cells mediates differential responses to fatty acids and is altered in obese mice"—*Gastroenterology*. 2014, April, 146(4), 995-1005; Dramane G et al., "Cell signaling mechanisms of gustatory perception of lipids: can the taste cells be the target of anti-obesity agents", *Curr; Med. Chem.* 2011, 18(22), 3417-22).

Moreover, recent studies have clearly shown that CD36 and GPR120 act as lipid-taste receptors in mice and human (Gilbertson T A, Khan N A. "Cell signaling mechanisms of oro-gustatory detection of dietary fat: advances and challenges." *Prog. Lipid. Res.* 2014, January, 53, 82-92). These observations raise the possibility of a $6^{th}$ taste modality, devoted to the perception of the fat, present in our diet. Interestingly, the GPR40, a GPCR, was detected in mice, but not in human fungiform taste buds (Matsumura S et al., "GPR expression in the rat taste bud relating to fatty acid sensing", *Biomed. Res.* 2007, Feb. 28, 49-55).

In addition, it has been observed that oro-sensory perception of dietary fat varies in individual, thus influencing nutritional status.

Indeed, it has been recently shown that there is a difference in the oro-sensory detection of fatty acids between lean and obese subjects. The threshold of gustatory perception of dietary lipids, such as oleic acid, is increased in obese subjects (Daoudi H et al., "Oral Fat Sensing and CD36 Gene Polymorphism in Algerian Lean and Obese Teenagers", *Nutrients.* 2015, Nov. 4, 7(11), 9096-9104). It has also been demonstrated that the genetic polymorphism of the CD36 gene correlates to a decrease in oro-sensory detection of dietary lipids in obese subjects (Mrizak I et al., "The A allele of cluster of differentiation 36 (CD36) SNP 1761667 associates with decreased lipid taste perception in obese Tunisian women. *Br. J. Nutr.* 2015, Apr., 28, 113(8), 1330-7). Consequently, the obese subjects have been considered as "hyposensitive" to detect dietary fatty acids and they will eat lipids in high quantity in order to regulate the "lipid-mediated" satiety. Similarly, obese mice, maintained on a high-fat diet, possess decreased lingual CD36 mRNA and protein levels. Hence, the decreased lingual CD36 expression in obese subjects would result in decreased signaling to brain and then to gut so as to control the satiety via the secretion of intestinal peptides/hormones. Therefore, the obese subjects eat more fat to trigger satiation.

Hence, several private companies and scientific groups have started to orient their R&D to elaborate a program on fat taste enhancers or fat taste agonists.

For instance, the publication of N. Godinot et al. ("Activation of tongue-expressed GPR40 and GPR120 by non-caloric agonists is not sufficient to drive preference in mice", *Neuroscience* 2013, 250, 20-30) describes six commercially available non-caloric agonists of GPR40 and two commercially available non-caloric agonists of GPR120 (compound 12 and compound 16, FIG. 1 of the same article). Godinot et al. assert the effects of these agonists as taste-triggering agents in mice.

However, they report that these agonists fail to initiate in mice a preference in the two-bottle preference tests with Intralipid (control) and the agonists, i.e.: intralipid is highly preferred, whereas mice do not show any preference for the tested agonists.

It is also known from the prior art, the document WO 2013/149031 that describes a powder flavor composition comprising a compound according to the formula (I) below or edible salt thereof, and at least one flavour co-ingredient wherein $R_1$ is an alkyl residue containing 6 to 20 carbon atoms, or an alkene residue containing from 9 to 25 carbon atoms with 1 to 6 double bonds, $R_1$ together with the carbonyl group to which it is attached is a residue of a carboxylic acid, and $NR_2R_3$, in which $R_3$ is H or together with $R_2$ and the N-atom to which they are attached, a 5-membered ring, is a residue of an amino acid, in particular a proteinogenic amino acid, ornithine, gamma-aminobutyric acid or beta alanine, or a 1-amino cycloalkyl carboxylic acid.

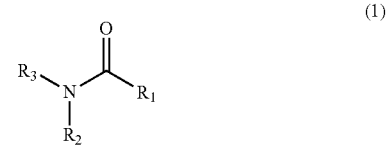

It is also known from the prior art the publication of Jose Antonio Cisneros et al. "Structure-Activity Relationship of a series of Inhibitors of Monoacylglycerol Hydrolysis-Comparison with Effects upon Fatty Acid Amide Hydrolas", *J. Med. Chem.* 2007, 50, 5012-5023, that describes a series of 32 heterocyclic analogues based on the structure of 2-arachidonoyglycerol (2-AG) which have been synthesized and tested for their ability to inhibit monoacylglycerol lipase and fatty acid amide hydrolase activities.

The publication of Sonyuan Lin et al. "Novel Analogues of Arachidonylethanolamide (Anandamide): Affinities for the CB1 and CB2 Cannabinoid Receptors and Metabolic Stability", *J. Med. Chem.* 1998, 41, 5353-5361, describes several analogues of the endogenous cannabinoid receptor ligand arachidonylethanolamide.

Hence, there is a need to develop new non-caloric, but palatable, compounds that can mimic natural caloric fatty acids and can trigger "fat-like taste", thus contributing to less dietary fat intake.

Therefore, there is a need in the art for providing new non-caloric compounds that act as agonists of the fast taste receptors, such as GPR120 and/or CD36, that is to say which are able to exhibit a similar or the same affinity as natural dietary fatty acids and which are able to strongly bind to these taste receptors so as to trigger fat-like taste without any caloric value.

There is also a need in the art that these non-caloric compounds are able to activate the GPR120 and/or CD36 receptors in order to trigger fast taste, this taste leading preferably to preference for these non-caloric compounds. There is indeed a need to provide palatable non-caloric agonists/analogues of GPR120 and/or CD36 receptors.

There is also a need in the art for an easily feasible and reproducible method for obtaining such non-caloric compounds.

It is also useful to develop therapeutic treatments to prevent and treat weight disorders and diseases linked to weight disorders, i.e.: obesity, type 2 diabetes, etc., and to develop cosmetic strategies to allow people who are in good health to stabilize a weight as low as possible as long as these values do not have a pathological character and/or to stay slim.

SUMMARY OF THE INVENTION

The present invention meets these needs since the inventors surprisingly discovered that some linoleic acid derivatives of formula (I) below are able to act as Fatty Acid Analogues (FAA), while being low-caloric and palatable.

Herein, FAA means a compound which acts as a natural dietary fatty acid, such as linoleic acid (LA), but with little caloric content and having a gustatory preference as or more than lipids.

Especially, the inventors have discovered that the linoleic acid derivatives of formula (I) are agonists of the orosensory fast-taste receptors CD36 and/or GPR120 which are involved in taste perception of dietary lipid. Hence, the linoleic acid derivative plays a role on the taste perception threshold of dietary lipids/fats.

As used herein, "agonist" means a chemical compound that binds or has affinity for the cellular receptors of another drug or natural substance and that produces a stimulatory physiologicaleffect.

The present invention thus provides linoleic acid derivatives of formula (I) below comprising a hydrophobic part $C_{17}H_{31}$ linked to a polar head part "A":

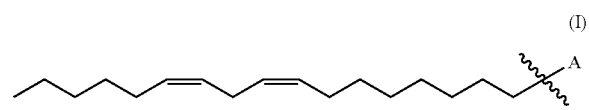

(I)

wherein said polar head part A is selected from $A^1$ to $A^4$ below:

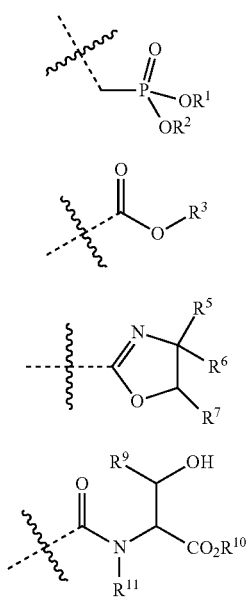

wherein $R^1$ and $R^2$ are independently selected from the group composed of H or a saturated or unsaturated, straight or branched alkyl group containing 1 to 8 carbon atoms, or $R^1$ and $R^2$ are linked together to form a divalent radical of formula —$R^1$-$R^2$—, wherein —$R^1$-$R^2$— is preferably —$CH_2$—$CH_2$— or —$(CH_2)_3$—;

$R^3$ is independently selected from the group composed of:

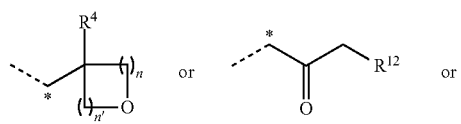

or

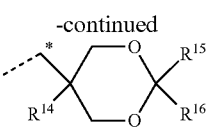

wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1, provided that $R^4$ is different from H when n=4 and n'=0 or when n=1 and n'=0, "*" is the carbon atom which is attached to the oxygen atom of the $A^2$ polar head;

$R^{12}$ is independently selected from the group composed of H or an alkyl group containing 1 to 4 carbon atoms, or an aromatic group, such as Ph, Tol, Xyl, or —$CO_2R^{13}$ in which $R^{13}$ is a saturated alkyl group containing 1 to 4 carbon atoms, $R^{14}$, $R^{15}$, $R^{16}$ is independently selected from H or $CH_3$, preferably $R^{14}$=$R^{15}$=$R^{16}$=$CH_3$ or $R^{14}$=H or $CH_3$ and $R^{15}$=$R^{16}$=H; and $R^5$, $R^6$ and $R^7$ are independently selected from the group composed of H or a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms, with the proviso that when $R^7$=H or $CH_3$, $R^5$ and $R^6$ are different from each other, especially when they correspond to $CH_3$ or to H;

$R^9$ to $R^{11}$ are independently selected from the group composed of H or a saturated or unsaturated, straight or branched alkyl group containing 1 to 4 carbon atoms provided that when $R^{10}$ and $R^{11}$=H, $R^9$ is different from an ethyl-group or H, or a pharmaceutically/food quality acceptable salt thereof.

As used herein, the term "pharmaceutically acceptable salt" refers to salt or complexes that retain the desired biological activity of the above described linoleic acid derivatives and exhibit minimal and no undesired toxicological effects. The "pharmaceutically acceptable salt" according to the invention includes therapeutically active, non-toxic base or acid salt forms, which the linoleic acid derivatives of formula (I) are able to form.

The term "food quality acceptable salt" used herein also refers to salt or complexes that retain the desired biological activity of the above described linoleic acid derivatives and exhibit minimal and no undesired toxicological effects. In addition, the "food quality acceptable salt" according to the invention includes cosmetic or non-therapeutic active, non-toxic base or acid salt forms, which the linoleic acid derivatives of formula (I) are able to form. The "food quality acceptable salt" according to the invention also means an edible compound, which is able to be eaten/ingested by an individual without any risk to his health. "Edible" used herein a consumable product, which can be eaten or ingested by the individual (advantageously a human or animal subject) without any risk to his health.

The use of these linoleic acid derivatives of formula (I) enables to contribute to curtailed dietary fat intake and, consequently, help combat pathologies, associated with weight disorders or dyslipidemia, such as obesity and obesity-associated type 2 diabetes, etc.

Hence, in other aspect, the invention relates linoleic acid derivatives of Formula (I) below comprising a hydrophobic part $C_{17}H_{31}$ linked to a polar head part "A":

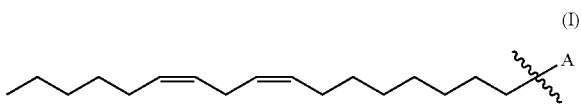
(I)

wherein said polar head part A is selected from $A^1$ to $A^4$ below:

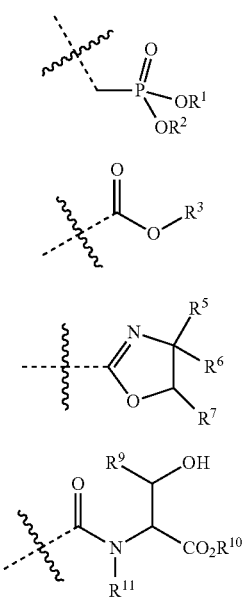

wherein $R^1$ and $R^2$ are independently selected from the group composed of H or a saturated or unsaturated, straight or branched alkyl group containing 1 to 8 carbon atoms, or $R^1$ and $R^2$ are linked together to form a divalent radical of formula —$R^1$-$R^2$—, wherein —$R^1$-$R^2$— is preferably —$CH_2$—$CH_2$— or —$(CH_2)_3$—;

$R^3$ is independently selected from the group composed of:

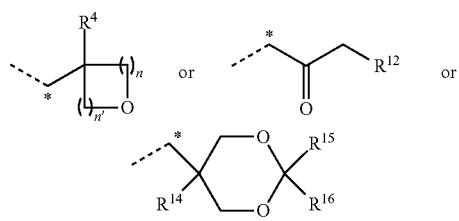

wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1; "*" is the carbon atom which is attached to the oxygen atom of the $A^2$ polar head; preferably $R^4$ is different from H when n=4 and n'=0 or when n=1 and n'=0;

$R^{12}$ is selected from H or a saturated or unsaturated, straight or branched alkyl group containing 1 to 4 carbon atoms, or an aromatic group or —$CO_2R^{13}$ in which $R^{13}$ is a saturated alkyl group containing 1 to 4 carbon atoms, and $R^{14}$, $R^{15}$, $R^{16}$ is independently selected from H or $CH_3$, preferably $R^{14}$=$R^{15}$=$R^{16}$=$CH_3$ or $R^{14}$=H or $CH_3$ and $R^{15}$=$R^{16}$=H;

$R^5$, $R^6$ and $R^7$ are independently selected from the group composed of H or a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms, preferably when $R^7$=H or $CH_3$, $R^5$ and $R^6$ are different from each other, especially when they correspond to $CH_3$ or to H;

$R^9$ to $R^{11}$ are independently selected from the group composed of H or a saturated or unsaturated, straight or branched alkyl group containing 1 to 4 carbon atoms, preferably when $R^{10}$ and $R^{11}$=H, $R^9$ is different from an ethyl-group or H;

or a pharmaceutically/food quality acceptable salt, for use as a medicament.

The invention also refers to a pharmaceutical composition comprising, at least one pharmaceutically acceptable carrier and at least one linoleic acid derivative such as described above in the section relative to the linoleic acid derivative for use as a medicament.

In addition, the present invention also refers to the linoleic acid derivatives defined above in the section relative to the linoleic acid derivative for use as a medicament or the pharmaceutical composition as described above for the use in the treatment of a disorder modulated by the GPR120 receptor and/or the CD36 receptor, comprising administering to a subject in need thereof a therapeutically effective amount of said linoleic acid derivative or of said pharmaceutical composition.

When used in the therapeutic treatment of excess weight, excess body fat, the linoleic acid derivatives according to the invention especially aim at people who are stressed or anxious, and/or having a diet with a high fat, and/or a sedentary lifestyle, and/or suffering from hormonal imbalances and/or from a genetic susceptibility to excess weight and/or obesity, and/or taking prescription drugs which can cause weight gain and/or being "hyposensitive" to detect dietary fatty acid due to, for instance, the genetic polymorphism of the CD36 and/or GPR120 genes which is different from the one of lean people.

In addition, the linoleic acid derivatives according to the invention may be used in food composition or as cosmetic treatment (i.e. non-therapeutic treatment) in lean or healthy people so as to improve their appearance.

Hence, in another aspect, the present invention relates to a food composition comprising, at least one food ingredient and/or at least one food additive and at least one linoleic acid derivative such as described above.

The invention also refers to a cosmetic use/non-therapeutic use of the linoleic acid derivatives such as described above or of the food composition such as described above, as taste enhancer, as taste modulator, or as appetite suppressant.

Such a cosmetic treatment is aimed at individuals whose weight and excess fat are not associated with a growing burden of disease and in particular at individuals who do not suffer from glucose metabolic disorders, insulin resistance, any metabolic syndrome, diabetes or vascular disorders.

The various embodiments of the present invention are especially described in the detailed specification hereafter. These embodiments may be considered separately or be combined with each other.

DETAILED DESCRIPTION OF THE INVENTION AND PREFERRED EMBODIMENTS

The terms "comprise" (and any grammatical variation thereof, such as "comprises" and "comprising"), "compose"

(and any grammatical variation thereof, such as "composed of), "have" (and any grammatical variation thereof, such as "has" and "having"), "contain" (and any grammatical variation thereof, such as "contains" and "containing"), and "include" (and any grammatical variation thereof, such as "includes" and "including") are open-ended linking verbs. They are used to specify the presence of stated features, integers, steps or components or groups thereof, but do not preclude the presence or addition of one or more other features, integers, steps or components or groups thereof. As a result, a method, or a step in a method, that "comprises," "compose", "has," "contains," or "includes" one or more steps or elements possesses those one or more steps or elements, but is not limited to possessing only those one or more steps or elements. In specific embodiments of the invention, each of these open-ended linking verbs can be independently interpreted as meaning "consisting of".

Unless otherwise indicated, all numbers or expressions referring to quantities of ingredients, ranges, reaction conditions, etc. used herein are to be understood as modified in all instances by the term "about."

Also unless otherwise indicated, the indication of an interval of values «from X to Y» or "between X to Y", according to the present invention, means as including the values of X and Y.

Linoleic Acid Derivatives According to the Invention (Faa Compounds)

As previously mentioned, the present invention relates to linoleic acid derivatives of formula (I) below comprising a hydrophobic part $C_{17}H_{31}$ linked to a polar head part "A":

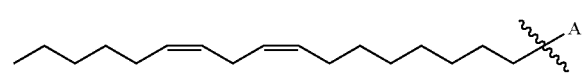

(I)

wherein said polar head part A is selected from $A^1$ to $A^4$ below:

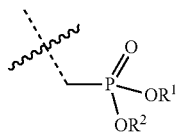

$A^1$

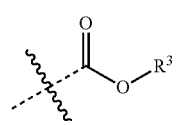

$A^2$

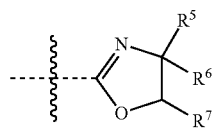

$A^3$

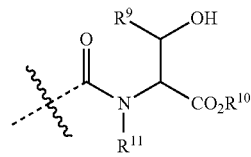

$A^4$ in which $R^1$ and $R^2$ are independently selected from the group composed of H or a saturated or unsaturated, straight or branched alkyl group containing 1 to 8 carbon atoms, or $R^1$ and $R^2$ are linked together to form a divalent radical of formula —$R^1$-$R^2$— preferably —$R^1$-$R^2$— is —$CH_2$—$CH_2$— or —$(CH_2)_3$—;

$R^3$ is independently selected from the group composed of:

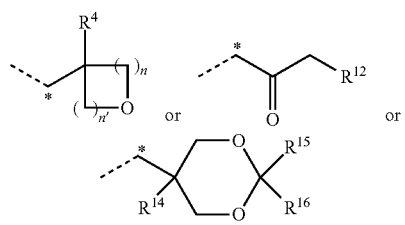

wherein $R^4$ is independently selected from the group composed of H or a saturated or unsaturated, straight or branched alkyl group containing 1 to 4 carbon atoms, n is an integer selected from 1 to 3, and n' is an integer that is equal to 0 or 1; provided that $R^4$ is different from H when n=4 and n'=0 or when n=1 and n'=0, "*" is the carbon atom which is attached to the oxygen atom of the $A^2$ polar head;

$R^{12}$ is independently selected from the group composed of H or an alkyl group containing 1 to 4 carbon atoms, or an aromatic group (such as Ph, Tol, Xyl) or —$CO_2R^{13}$ in which $R^{13}$ is a saturated alkyl group containing 1 to 4 carbon atoms, $R^{14}$, $R^{15}$, $R^{16}$ is independently selected from H or $CH_3$, preferably $R^{14}$=$R^{15}$=$R^{16}$=$CH_3$ or $R^{14}$=H or $CH_3$ and $R^{5}$=$R^{16}$=H; and $R^5$, $R^6$ and $R^7$ are independently selected from the group composed of H, a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms, with the proviso that when $R^7$=H or $CH_3$, $R^5$ and $R^6$ are different from each other, especially when they correspond to $CH_3$ or to H;

$R^9$ to $R^{11}$ are independently selected from the group composed of H or a saturated or unsaturated, straight or branched alkyl group containing 1 to 4 carbon atoms provided that when $R^{10}$ and $R^{11}$=H, $R^9$ is different from an ethyl-group or H, or a pharmaceutically/food quality acceptable salt thereof.

Hereafter, the linoleic acide derivative of formula (I) according to the invention are also called "FAA compounds".

In addition, the FAA compounds according to the invention are considered as GRAS (Generally Recognized As Safe) since they derive from naturally available dietary fatty acid, i.e. linoleic acid (LA) of formula (I) below.

Formula (II)

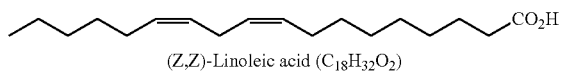

(Z,Z)-Linoleic acid ($C_{18}H_{32}O_2$)

Indeed, the hydrophobic part of all the FAA compounds according to the invention is identical ($C_{17}H_{31}$) to the one of the LA compound: the carbon-length or the methyl-terminal of LA has not been changed or amended to form the FAA compounds according to the invention. Only, the carboxylic (—$CO_2H$) terminal part has been changed by different prosthetic groups forming the polar head part A of the FAA compounds $A^1$ to $A^4$.

Thus, the different FAA compounds according to the invention all share a significant structural element, which is a common chemical structure which occupies a large portion of their structures, that is to say: the hydrophobic part $C_{17}H_{31}$. Moreover, according to the present invention, the FAA compound may have a molecular weight which is close to the one of the linoleic acid, that is to say close to 280 g/mol. Especially, the FAA compound according to the invention has a molecular weight ranging from about 300 to about 600 g/mol, preferably ranging from 300 to 400 g/mol.

According to the invention, "a molecular weight ranging from about 300 to about 600 g/mol" comprises the followings values: 300; 310; 320; 330; 333; 334; 335; 336; 337; 338; 339; 340; 341; 342; 343; 344; 345; 346; 347; 348; 349; 350; 351; 352; 353; 354; 355; 356; 357; 358; 359; 360; 361; 362; 363; 364; 365; 366; 367; 368; 369; 370; 371; 372; 373; 374; 375; 376; 377; 378; 379; 380; 381; 382; 383; 384; 385; 386; 387; 388; 389; 390; 391; 392; 393; 394; 395; 396; 397; 398; 399; 400; 410; 420; 430; 440; 450; 460; 470; 480; 490; 500; 510; 520; 530; 540; 550; 560; 570; 580; 590; 600 and all intervals included between these values.

In general, these FAA compounds are synthesized from linoleic acid, typically technical linoleic acid.

In addition, as it will be described below in the Example part, all these different FAA compounds have a common property. Indeed, they are able to bind to fat taste receptors, such as CD36 and/or GPR120.

Therefore, these different FAA compounds according to the invention have similar nature and hence form a single invention.

The Applicant has surprisingly discovered that these specific FAA compounds are able to target the lingual fat taste receptors CD36 and/or GPR120 (in general both CD36 and GPR120) involved in the gustatory perception of dietary lipids. In addition, the Applicant has also discovered that these compounds possess fat-like taste. Besides, the Applicant also observed that at least two FAA compounds, i.e., NKS-3 and NKS-5 tested below, triggered attraction in mice, in a two-bottle preference test, at 140 and 93 times, respectively, higher concentrations than LA which was preferred by these animals at 7.13 mM or 0.2% (see FIG. 5, FIG. 6A, FIG. 7A). Indeed, FAA compounds exhibit a high or the same affinity as natural fatty acids, such as linoleic acid and bind strongly to taste receptors and, consequently, trigger fat-like taste without any or very few caloric value.

In support of that view, freshly isolated and primary cultured mice type II taste bud cells (expressing GPR120 and CD36) are used. These cells also express functional receptors of other five taste modalities (bitter, sweet, salt, acid, umami). It has been demonstrated that at least two of the FAA compounds according to the invention are biologically active. One compound termed as NKS-3 bound to CD36, whereas another NKS-5 binds both to CD36 and GPR120. These two compounds NKS-3 and NKS-5, in mouse taste bud cells, induce, similar to linoleic acid (LA), a rapid and significant rise in calcium signaling, considered as one of the earliest events in taste perception (FIGS. 1 to 4). These two compounds also trigger a "taste-like" sensation in a two-bottle preference test in mice (FIG. 5, FIG. 6A and FIG. 7).

As it will be described below, the FAA compounds according to the invention may be used to decrease circulating lipids in other pathophysiological situations. It is noteworthy that a reduction in the consumption of products rich in saturated fatty acids is advised to the subjects, suffering from obesity or the pathologies related to dyslipidemia, such as atherosclerosis, hypertension, diabetes type II, etc.

The compounds $A^1$-$A^4$ of the invention are derived from linoleic acid (LA) (scheme 1 below).

Their synthesis is based either on the condensation of linoleic acid with alcohols $R^3OH$, β-amino alcohols or p-hydroxyamino esters to afford the compounds $A^2$, $A^3$ or $A^4$, respectively (Scheme 1a-c). On the other hand, the compounds A were synthesized by alkylation of dialkylphosphite with the octadecadienyl bromide ($C_{18}H_{33}Br$) previously prepared from LA by subsequent reduction and halogenation reactions (Scheme 1d). Experimental parts are reported for all compounds in the example part below.

Scheme 1

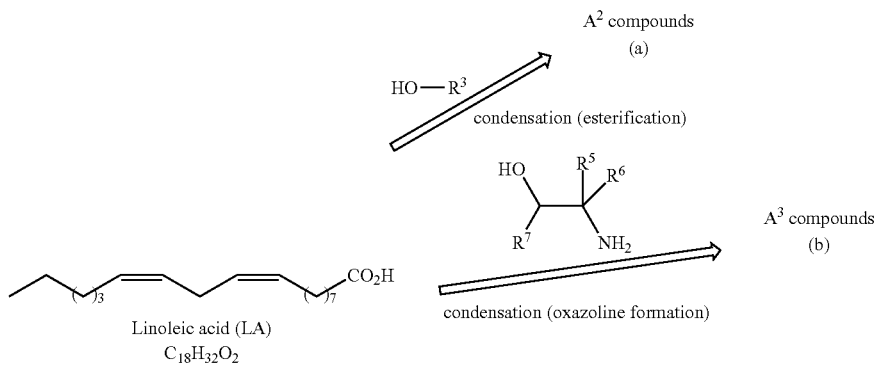

-continued

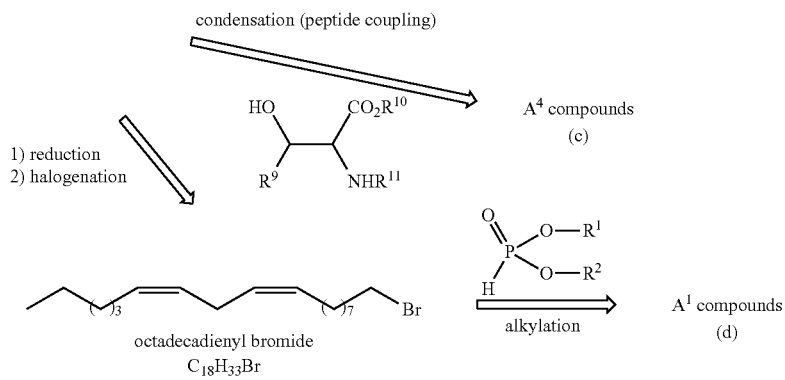

According to a first embodiment of the invention, the polar head "A" of the FAA compound has a phosphorus group and may be selected from the group $A^1$:

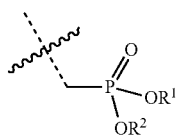

$A^1$ wherein $R^1$ and $R^2$ are independently selected from the group composed of H or a saturated or unsaturated, straight or branched alkyl group containing 1 to 8 carbon atoms, preferably 1 to 5 carbon atoms and typically 2 to 4 carbon atoms, or $R^1$ and $R^2$ are linked together to form a divalent radical of formula —$R^1$-$R^2$— preferably —$R^1$-$R^2$— is —$CH_2$—$CH_2$— or —$(CH_2)_3$—.

In general, $R^1$ and $R^2$ may be straight alkyl group containing 1 to 8 carbon atoms, preferably 1 to 5 carbon atoms and typically 2 to 4 carbon atoms, or $R^1$ and $R^2$ are linked together to form a divalent radical of formula —$R^1$-$R^2$— preferably —$R^1$-$R^2$— is —$CH_2$—$CH_2$— or —$(CH_2)_3$—.

Especially, in this embodiment, $R^1$ and $R^2$ of $A^1$ may be a saturated or unsaturated, straight or branched alkyl group containing 1 to 2 carbon atoms, or a pharmaceutically/food quality acceptable salt thereof.

Typically, $R^1$ and $R^2$ of $A^1$ are ethyl group so as to form the diethyl (9Z,12Z)-octadeca-9,12-dien-1-ylphosphonate, Called Hereafter "NKS-3" compound corresponding to the formula (III) below:

Formula (III)

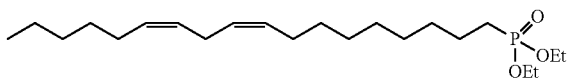

NKS3

According to this embodiment, $R^1$ and $R^2$ of $A^1$ may be butyl group so as to form the dibutyl (9Z,12Z)-octadeca-9,12-dien-1-ylphosphonate, Called Hereafter "1f", corresponding to the formula (IV) below:

Formula (IV)

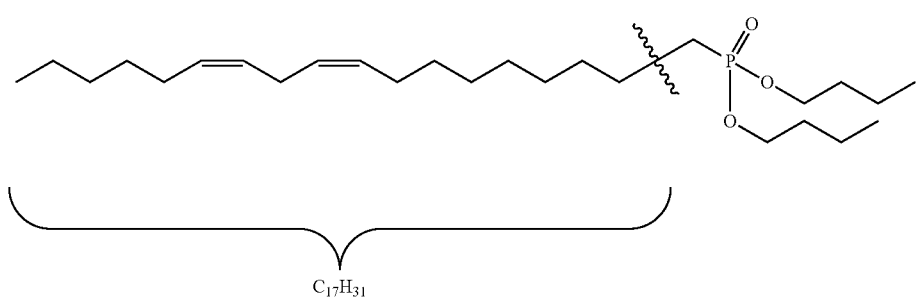

1f $R^1$ and $R^2$ of $A^1$ may be also linked together to form a divalent radical of formula —$R^1$-$R^2$— wherein —$R^1$-$R^2$— is —$CH_2$—$CH_2$—, Called Hereafter "1g", so as to form the compound corresponding to the formula (V) below:

Formula (V)

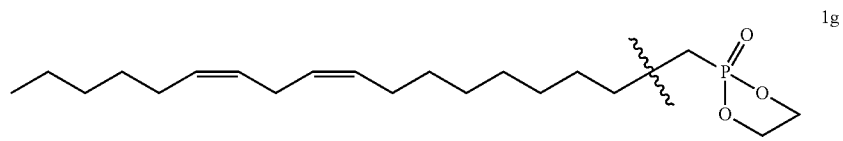

These differents FAA organophosphorus compounds may be prepared from linoleic acid (LA) by alkylation of dialkylphosphite 5 with the octadecadienyl bromide previously prepared by subsequent reduction of LA with $LiAlH_4$ then bromation with a mixture $PPh_3/CBr_4$ (Scheme 2).

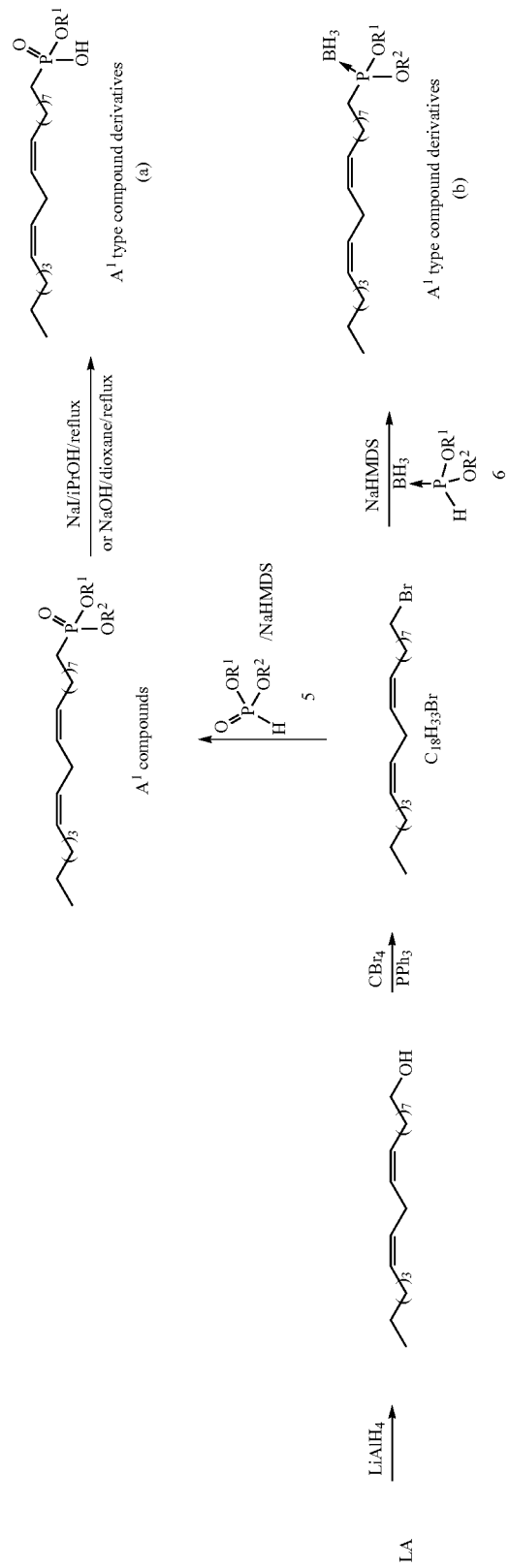
Scheme 2

It should be noted that the A compounds could be saponified by heating at reflux a mixture of NaI in isopropanol or NaOH in dioxane, to afford the corresponding $A^1$ derivative as a mono acid phosphonic: i.e. bearing a —$P(O)OR^1OH$ as polar group (Scheme 2a).

In addition, FAA organophosphorus $A^1$ compounds must also be prepared by alkylation of dialkylphosphonous borane complex 6 with the bromide ($C_{18}H_{33}Br$) derived from LA (Scheme 2b).

Moreover, the synthesis of derivatives such as $A^1$ has been envisaged by keeping in consideration that a FAA should be isosteric (function as an ester) in the hydrolysis transition state inside the receptor site.

According to a second embodiment of the invention, the polar head "A" of the FAA compound may be selected from the group $A^2$:

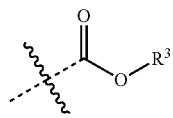

$R^3$ is independently selected from the group composed of:

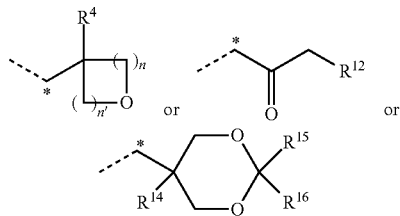

wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1, provided that $R^4$ is different from H when n=4 and n'=0 or when n=1 and n'=0; "*" is the carbon atom which is attached to the oxygen atom of the $A^2$ polar head;

$R^{12}$ is independently selected from the group composed of H or an alkyl group containing 1 to 4 carbon atoms, or an aromatic group (such as Ph, Tol, Xyl) or —$CO_2R^{13}$ in which $R^{13}$ is a saturated alkyl group containing 1 to 4 carbon atoms, and $R^{14}$, $R^{15}$, $R^{16}$ is independently selected from H or $CH_3$, preferably $R^{14}=R^{15}=R^{16}=CH_3$ or $R^{14}=H$ or $CH_3$ and $R^{15}=R^{16}=H$.

According to a preferred first aspect of this embodiment, when n=1 to 4 and n'=0 or 1, $R^3$ is an oxacycloalkane group:

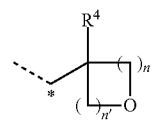

In general, according to this embodiment, $R^4$ is preferably $CH_3$ or H.

Especially, according to this embodiment, $R^4$ is different of H when n=4 and n'=0 or when n=1 and n'=0.

For instance, $R^4$ may be $CH_3$ and n=n'=1 and may correspond to the following compound, called hereafter NKS-5 compound responding to the formula (VI) below, or a pharmaceutically/food quality acceptable salt thereof.

Formula (VI)

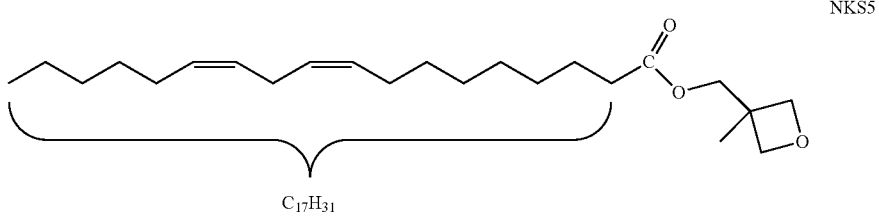

Also, according to this embodiment, $R^4$ may be H and n=2 and n'=1, or a pharmaceutically/food quality acceptable salt thereof, Called Hereafter "1a" compound corresponding to the formula (VIIa) below:

Formula (VIIa)

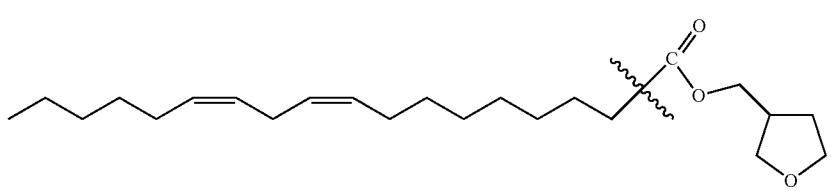

Alternatively of Formula (VIIa), when n=2 and n'=1, $R_4$ is different from H and corresponds to a saturated or unsaturated, straight or branched alkyl group containing 1 to 4 carbon atoms, such as $CH_3$.

According also to this embodiment, $R^4$ may be H and n=3 and n'=0 respectively, or a pharmaceutically/food quality acceptable salt thereof, Called Hereafter "1x" compound corresponding to the formula (VIIb) below:

Formula (VIIb)

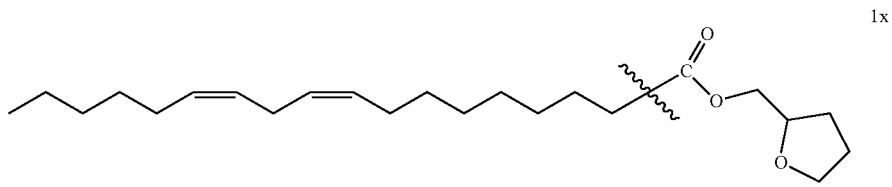

Especially, $R^4$ may be H and n and n' may be 1, or a pharmaceutically/food quality acceptable salt thereof, Called Hereafter "1b" compound responding to the formula (VIII) below:

Formula (VIII)

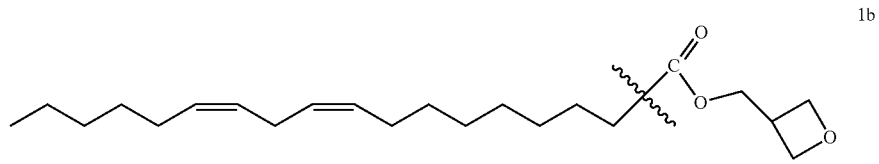

According to a characteristic of this embodiment, $R^4$ may be H and n may be 1 and n' may be 0, or a pharmaceutically/food quality acceptable salt thereof, Called Hereafter "1c" compound responding to the formula (IX) below:

Formula (IX)

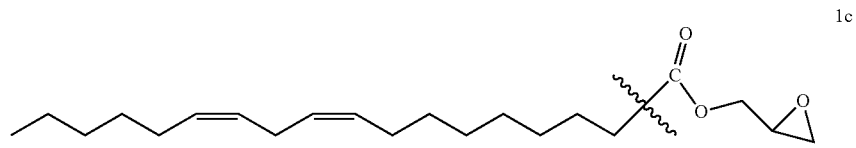

According to another characteristic of this embodiment, when n=1 and n'=0, $R^4 \neq H$ and is preferably a saturated or unsaturated, straight or branched alkyl group containing 1 to 4 carbon atoms.

According to a preferred second aspect of this embodiment of the polar head $A^2$, $R^3$ may be:

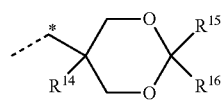

Formula (X)

in which $R^{14}$, $R^{15}$, $R^{16}$ is independently selected from H or $CH_3$, preferably $R^{14}=R^{15}=R^{16}=CH_3$ or $R^{14}=H$ or $CH_3$ and $R^{15}=R^{16}=H$;

or a pharmaceutically/food quality acceptable salt thereof. In particular, $R^3$ may be:

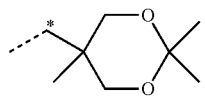

or a pharmaceutically/food quality acceptable salt thereof, Called Hereafter "1d" compound responding to the formula (X) below:

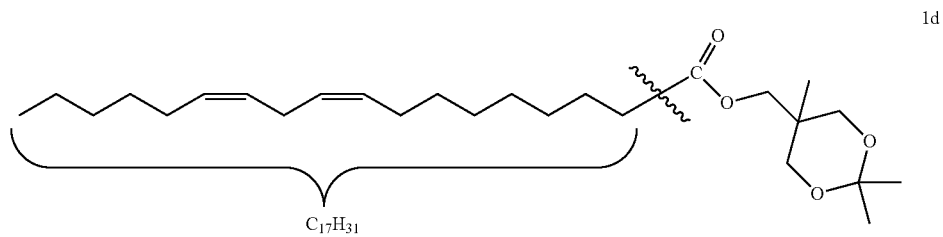

According to a preferred third aspect of this embodiment relating to the polar head $A^2$, $R^3$ may be derivated from an alpha-hydroxyketone group:

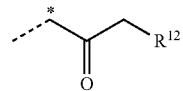

and $R^{12}$ is selected from H or alkyl group containing 1 to 4 carbon atoms, or an aromatic group (such as Ph, Tol, Xyl) or $-CO_2R^{13}$ in which $R^{13}$ is a saturated alkyl group containing 1 to 4 carbon atoms, or a pharmaceutically/food quality acceptable salt thereof.

For instance, for $R^{12}=H$, the following compound is obtained, Called Hereafter "1e" compound responding to the formula (XI) below:

Formula (XI)

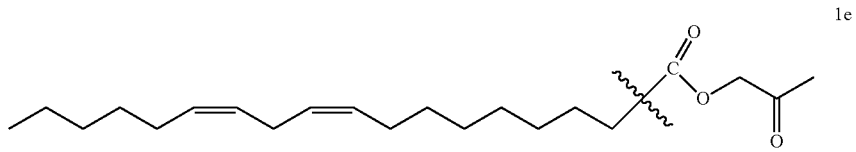

According to a third embodiment of the invention, the polar head "A" of the FAA compound may be selected from the group $A^3$:

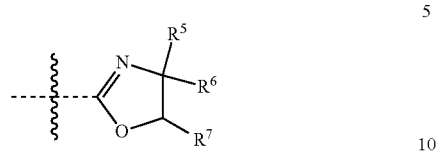

wherein $R^5$, $R^6$ and $R^7$ are independently selected from the group composed of H, a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms, with the proviso that when $R^7$=H or $CH_3$, $R^5$ and $R^6$ are different from each other, especially when they correspond to $CH_3$ or to H.

According to the invention, when $R^7$=H or $CH_3$, $R^5$ and $R^6$ are different from each other, especially when they correspond to $CH_3$ or to H.

Preferably, when $R^5$=$R^7$=H, $R^6$ is different from H.

Especially in this embodiment, $R^5$ may be H, $R^6$ may be —$CO_2CH_3$ and $R^7$ may be H, or a pharmaceutically/food quality acceptable salt thereof, so as to form the following FAA compound of formula (XII):

Formula (XII)

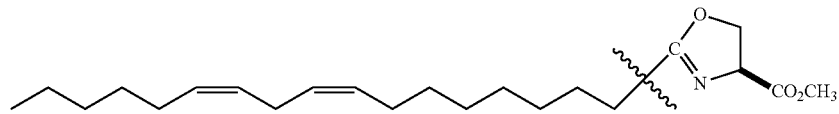

Also, according to a characteristic of this embodiment, $R^5$ may be $CH_3$, $R^6$ may be $CH_3$ and $R^7$ may be H, or a pharmaceutically/food quality acceptable salt thereof, so as to form the following FAA compound (2-((8Z,11Z)-heptadeca-8,11-dien-1-yl)-4,4-dimethyl-4,5-dihydro oxazole) of formula (XIII) below:

Formula (XIII)

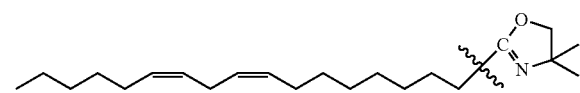

According to a fourth embodiment of the invention, the polar head "A" of the FAA compound may be selected from the group $A^4$:

wherein $R^9$ to $R^{11}$ are independently selected from the group composed of H or a saturated or unsaturated, straight or branched alkyl group containing 1 to 4 carbon atoms provided that when $R^{10}$ and $R^{11}$=H, $R^9$ is different from an ethyl-group or H, or a pharmaceutically/food quality acceptable salt thereof.

Especially in this embodiment, $R^9$ is H, $R^{10}$ is $CH_3$, and $R^{11}$ is H, or a pharmaceutically/food quality acceptable salt thereof, so as to form the following FAA compound (S)-methyl 3-hydroxy-2-((9Z,12Z)-octadeca-9,12-dienamido) propanoate of formula (XIV):

Formula (XIV)

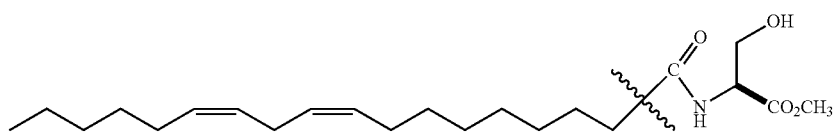

According to a characteristic of this embodiment, in general, $R^9$ and $R^{10}$ are different especially when one of this group is H. In addition, generally, when $R^9$=H, $R^{10}$ w ethyl group.

According to the invention, when $R^{10}$ and $R^{11}$=H, $R^9$ is different from an ethyl-group or H.

The synthesis of compounds such as $A^2$ to $A^4$ from linoleic acid has been carried out, by employing protective reagents well-tolerated by the organism such as alcohols, aminoalcohols, or hydroxyamino esters, with the aim of obtaining derivatives or metabolites presenting no risk to health. Their synthesis is based either on the condensation of linoleic acid with alcohols $R^3OH$, β-amino alcohols or p-hydroxyamino esters to afford the compounds $A^2$, $A^3$ or $A^4$, respectively (Scheme 1).

In particular, the FAA compound according to the invention is NKS-3, NKS-5 or combination thereof.

The FAA compound may be in a great plurality galenic form, such in a liquid form or in the form of a capsule, dragee, pill, powder, suppository, or any other galenic formulation.

Human and Animal Pharmaceutical Composition According to the Invention

As previously mentioned, these FAA compounds described above, once in the mouth cavity of an individual or an animal, advantageously would trigger fat-like taste and can be used to reduce fat contents in the diet.

Therefore, the invention also refers to FAA compounds (linoleic acid derivatives) of Formula (I) below comprising a hydrophobic part $C_{17}H_{31}$ linked to a polar head part "A":

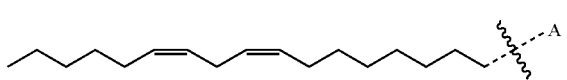

(I)

wherein said polar head part A is selected from $A^1$ to $A^4$ below:

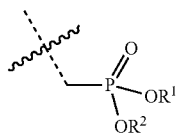

$A^1$

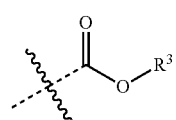

$A^2$

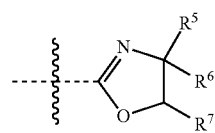

$A^3$

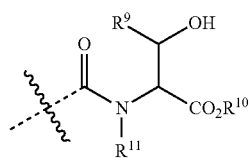

$A^4$ wherein $R^1$ and $R^2$ are independently selected from the group composed of H or a saturated or unsaturated, straight or branched alkyl group containing 1 to 8 carbon atoms, or $R^1$ and $R^2$ are linked together to form a divalent radical of formula —$R_1$-$R_2$—, wherein —$R_1$-$R_2$— is preferably —$CH_2$—$CH_2$— or —$(CH_2)_3$—;

$R^3$ is independently selected from the group composed of:

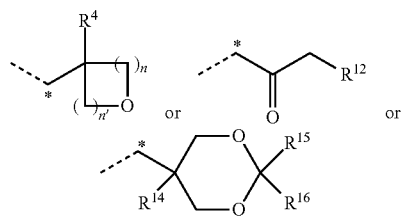

wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1; "*" is the carbon atom which is attached to the oxygen atom of the $A^2$ polar head; preferably $R^4$ is different from H when n=4 and n'=0 or when n=1 and n'=0;

$R^{12}$ is selected from H or a saturated or unsaturated, straight or branched alkyl group containing 1 to 4 carbon atoms, or an aromatic group or —$CO_2R^1$ in which $R^{13}$ is a saturated alkyl group containing 1 to 4 carbon atoms, and $R^{14}$, $R^{15}$, $R^{16}$ is independently selected from H or $CH_3$, preferably $R^{14}$=$R^{15}$=$R^{16}$=$CH_3$ or $R_{14}$=H or $CH_3$ and $R^{15}$=$R^{16}$=H;

$R^5$, $R^6$ and $R^7$ are independently selected from the group composed of H or a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms, preferably when $R^7$=H or $CH_3$, $R^5$ and $R^6$ are different from each other, especially when they correspond to $CH_3$ or to H;

$R^9$ to $R^{11}$ are independently selected from the group composed of H or a saturated or unsaturated, straight or branched alkyl group containing 1 to 4 carbon atoms, preferably when $R^{10}$ and $R^{11}$=H, $R^9$ is different from an ethyl-group or H;

or a pharmaceutically/food quality acceptable salt or such as described above in the description of the linoleic acid derivatives as such (above-mentioned part), for use as a medicament.

Of course, the characteristics of the linoleic acid derivatives described above are here included for the description of the pharmaceutical composition or the use of the linoleic acid derivatives as a medicament.

According to the first aspect, a pharmaceutical composition according to the present invention comprises as active compound at least one linoleic acid derivative (FAA compound) such as described above or one pharmaceutically salt thereof, in an amount suitable for treating a disorder modulated by the GPR120 receptor and/or the CD36 fat taste receptor in individuals in need of such treatment.

In general, the disorder modulated by the GPR120 receptor and/or the CD36 receptor is selected from the group consisting of: diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, body weight disorder, fatty liver disease, dyslipidemia, hyperlipidemia, hypertriglyceridemia, hypercholesterolemia, low high-density lipoprotein (HDL), high low-density lipoprotein (LDL), lipid disorders and liver diseases such as NASH (Non-Alcoholic SteatoHepatitis), NAFLD (Non-Alcoholic Fatty Liver Disease) and liver cirrhosis, dyslipidemia, artheroslerosis and cachexia.

The Applicant considers that a significant reduction of lipids can be envisaged by using FAA compounds according to the invention. A reduction in lipids, even of 25% in human daily diet, would be beneficial for instance for pathological dyslipidemia.

According to the second aspect, a pharmaceutical composition according to the present invention is useful as agonist of fat taste receptor GPR120 and/or CD36.

According to the third aspect, a pharmaceutical composition according to the present invention is useful as appetite suppressant.

Preferably, a FAA compound of the invention or the pharmaceutical composition is administered by mouth (oral administration).

Suitable forms for oral route are for example tablets, hard gelatin capsules, lozenges, powders, granules, lyophilizates, oral solutions and syrups. Tablets, powders, granules, lyophilizates, oral solutions and syrups represent the currently most preferred pharmaceutical or cosmetic form adapted to oral administration. If a solid composition in the form of tablets should be prepared, it would be possible for example to combine the FAA compound with a physiologically acceptable vehicle such as gelatin, starch, lactose, magnesium stearate, talc, gum arabic or equivalents. Tablets may be of various types, providing an immediate release, or a controlled or a slow release, and optionally be in an effervescent or oro-dispersible form.

Gelatin capsules may be obtained by combining the FAA compound with a diluent and pouring the resulting mixture into soft or hard capsules.

A preparation in the form of syrup or elixir may for example contain the FAA compound with a suitable sweetener, antiseptic agent, preservative, flavoring agent or coloring agent.

Powders, lyophilizates or granules that are dispersible in water may contain the FAA compound in admixture with dispersing agents or wetting agents or suspending agents, as well as with taste modifiers or sweeteners.

In its form suitable for human administration, a pharmaceutical composition according to the present invention advantageously comprises at least one FAA compound or one pharmaceutically salt thereof in an amount suitable for a daily administration of the active compound.

In its form suitable for animal administration, a pharmaceutical composition according to the present invention comprises FAA compound in an amount suitable for a daily administration.

A pharmaceutical composition according to the present invention comprises FAA compound in association with at least one excipient selected from the pharmaceutically acceptableexcipients.

Physiologically acceptable adjuvants, vehicles and excipients are also described in "Handbook of Pharmaceutical Excipients", Second edition, American Pharmaceutical Association, 1994.

To formulate a pharmaceutical composition according to the present invention, the man skilled in the art will advantageously refer to the last edition of the European Pharmacopoeia or the American Pharmacopoeia (USP).

Food Composition

As previously mentioned, such FAA compound according to the invention could also be used within the framework of a non-therapeutic or cosmetic use (or method) in the form of a food composition in people who are in good health, that is to say whose weight and/or excess body fat are not associated with a growing burden of disease.

As used herein, "people in good health" preferably mean individuals who have a corpulence considered as normal according to the WHO standards. When used with a cosmetic approach, said FAA compound of the invention will preferably be proposed in a form that is adapted to oral administration, as for example a food supplement or a functional food.

The present invention also relates food composition comprising, at least one food ingredient and/or at least one food additive and at least one FAA compound such as described above.

Of course, the characteristics of the linoleic acid derivative described above are here included for the description of the food composition.

In a first aspect of the invention for instance as supplement food, the food composition according to the present invention comes is in different galenic form, such as liquid form or in the form of a capsule, dragee, pill, powder, suppository, or any other galenic formulation.

As used herein, a "food supplement" means a preparation that is intended to supply a nutrient that is missing from a diet, and here especially, which may replace natural fatty acid.

In a second aspect of the invention, for instance as functional food, the food composition according to the present invention comes is in a great plurality of food and beverage forms, comprising juices (fruits or vegetables), oils, butters, margarines, vegetal fats, cans (for example tuna fish in oil), soups, milk-based preparations (yogurts, cottage cheese), ice creams, cheeses (for example oil-kept cheeses), baked products (such as bread, cookies and cakes), puddings, confectionary products, cereal bars, breakfast cereals, condiments, seasoning products (especially spices and dressings).

As used herein, a "functional food" is intended to mean any food or beverage, for example, milk products from animal origin (butter, cheese, yogurt, milk) or from vegetable origin (milk, yogurt, cereals, fruit or vegetable juices, soups, etc.) to which a combination product of the invention has been added. Preferably, said FAA compound then comes as a single composition added to food, as previously mentioned.

Generally, the food composition according to the present invention comes as any form, and in particular fat-base food products (butter, oil, margarine), bread, cookies, or oil kept food products, such as cheese, fish, meat, vegetables, or salads) or as seasoning products, such as condiments.

Preferably, a food composition according to the present invention comprises the FAA compound or one salt thereof in an amount suitable for a daily oral administration.

For human supply, a food composition according to the present invention comprises an amount of active compound suitable for a daily supply of FAA compound or one salt thereof provided by said composition.

For animal supply, specifically a non-human mammalia, a food composition according to the present invention is suitable for a daily administration of active compound provided by said composition.

As used herein, a "food additive" useful according to the invention may be:
- vitamins, such as vitamin A, vitamin D, vitamin E, vitamin K, vitamin C, folic acid, thiamine, riboflavin, vitamin B6, vitamin B12, niacin, biotin or panthothenic acid;
- minerals such as sodium, potassium, phosphorus, magnesium, copper, zinc, iron, selenium, chromium and molybdenum;
- soluble fibers such as agar-agar, alginate, locust bean, carragheenan, acacia gum, guar gum, karaya gum, pectin or xanthan gum, such soluble fibers being in hydrolyzed or non-hydrolyzed form;
- energetic source compounds, especially one or more carbon hydrate source(s) selected from the group consisting of maltodextrins, starch, lactose, glucose, sucrose, fructose, xylitol and sorbitol and optionally fatty acids such as omega-3;
- prebiotic, probiotic,
- antioxidant,
- flavonoids,
- spices or aromatic herbs.

As used herein, a "food ingredient" useful according to the invention may be selected among fruit, vegetables, meat, fish, cereal, etc. or one of their combination.

The present invention also relates in one aspect to a food composition such as described above used under a form selected from: food supplement or dietary supplement for animal or human food, or ready-cooked dish, or animal feedstuff.

The present invention further relates to a cosmetic use of the linoleic acid derivative described above or of the food composition described above for improving the appearance of individuals, for example for slimming the figure and/or reducing or restraining localized fat accumulations or lipodystrophy, and/or for stimulating the loss of excess weight and/or of cellulite, and/or for limiting the accumulation thereof, in individuals who are in good health.

As used herein, treating "excess weight" is intended to mean that said cosmetic method is aimed at subjects (humans or animals, for example pets, farmed animals, sport-related animals or animals dedicated to shows) with a normal corpulence. In humans for example, people will be considered, who are in good health, the excess weight or fat accumulation of whom is not associated with pathological conditions or a growing burden of disease (typically glucose metabolism disorders, insulin resistance, metabolic syndrome, diabetes or vascular disorders) and the BMI of whom is from 18.5 to 25. In these subjects, excess weight or body fat typically exist as cellulite, is not associated with a growing burden of disease and is preferably distributed according to a gynoid pattern. A cosmetic treatment according to the present invention will therefore be especially suited to the treatment of cellulite, in particular on hips and buttock. It could be used for example in women who go through menopause or after pregnancy and, as a rule, in individuals having a sedentary lifestyle and/or a diet that is high in sugar or in fat, so as to contribute to preserve or to rediscover a slim body and to remove or prevent the development of cellulite. Such a treatment may also be useful in castrated animals so as to prevent the increase in body fat at the cost of muscular lean mass.

Weight loss is often induced through restrictive diets, that are hard to observe in the long term and that are frequently responsible for a so called rebound effect (or relapse) with, as a consequence, a new weight gains sometimes higher than the one induced through the caloric restriction itself. A cosmetic treatment method according to the present invention could thus be used as a complement to a restrictive diet while optionally increasing physical activity, so as to limit the intensity of the restriction, especially the caloric one, and so as to prevent any lean body mass loss and rebound effect when stopping the restrictive diet.

A cosmetic (i.e. non-therapeutic) use according to the present invention comprises the administration of the FAA compound according to the invention, preferably by oral administration.

Most preferably, the cosmetic use or food composition is adapted to oral administration and is intended to be taken as a food supplement such as previously described.

In other aspect, the present invention also relates to the cosmetic use of the linoleic acid derivative described above or of the food composition described above:
- as taste enhancer, as taste modulator, as appetite suppressant;
- for improving the physical look of individuals, for example for body slimming and/or reducing or restraining localized fat accumulations or lipodystrophy, and/or for stimulating the loss of excess weight and/or of cellulite, and/or for limiting the accumulation thereof, in individuals who are in good health.

DESCRIPTION OF THE FIGURES

The present invention will be hereafter illustrated without being limited thereto by means of the following examples. It will be referred to the following figures in the examples:

FIG. 3: Measurements of intracellular $Ca^{2+}$ in freshly isolated taste bud cells.

FIG. 4: Measurements of intracellular $Ca^{2+}$ in freshly isolated taste bud cells; especially

FIG. 6: Gustatory preference for the linoleic acid derivative NKS-3 according to the invention in a two bottle-preference test.

EXAMPLES

Figure 1A:
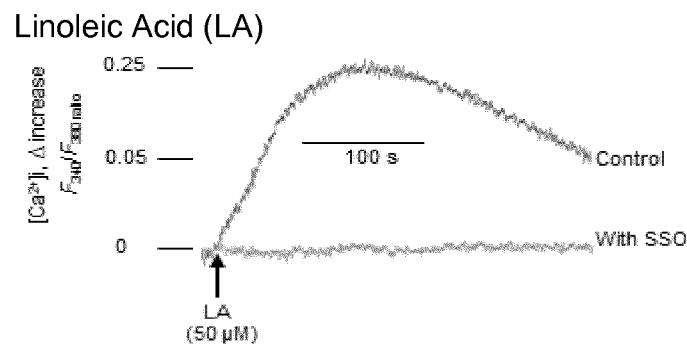
FIG. 1: Action of the CD36 inhibitor (20 µM SSO, Sulfo-N-succinimidyl Oleate) on the increase in intracellular free calcium concentrations, $[Ca^{2+}]i$, by linoleic acid (LA) as control test (FIG. 1A) and different linoleic acid derivatives according to the invention: NKS-3 (FIG. 1B) and NKS-5 (FIG. 1C) in mouse taste bud cells. The SSO completely blocked the responses triggered by LA and NKS-3, whereas the response of NKS-5 was partially inhibited by this blocker.

1. Synthesis of Different Linoleic Acid Derivatives of the Invention 1.1 Synthesis of methyl (S)-3-hydroxy-2-((9Z,12Z)-octadeca-9,12-dienamido)propanoate, Called Hereafter "NKS-2"

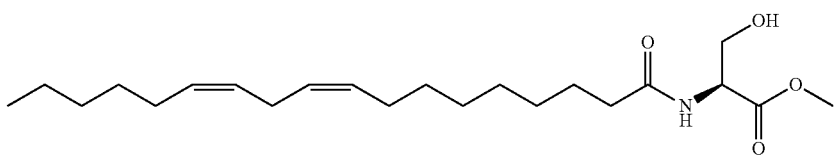

(S)-methyl 3-hydroxy-2-((9Z, 12Z)-octadeca-9, 12-dienamido)propanoate
Chemical Formula: $C_{22}H_{39}NO_4$
Molecular Weight: 381.55

In a Schlenk were introduced linoleic acid (0.93 mL, 3.0 mmol), tetrahydrofyran (THF) (45 mL), L-serine methyl ester hydrochloride (0.47 g, 3.0 mmol) and (Benzotriazol-1-yloxy)tripyrrolidinophosphonium hexafluorophosphate (PyBOP) (1.75 g, 3.3 mmol). The suspension was treated with iPr$_2$NEt (1.150 mL, 6.6 mmol) and stirred for 4 h at room temperature. Solvent was removed under vacuum and the residue was dissolved in ethyl acetate (EtOAc). The organic phase was successively treated by HCl 1M, water, saturated aqueous NaHC$_3$, water and brine. The organic layer was concentrated and the product purified by column chromatography on SiO$_2$ (petroleum ether/ethyl acetate (1:3)). $m_{pure}$=0.87 g. Aspect: colorless oil. Yield: 76%.

$^1$H NMR (500 MHz, CDCl$_3$) δ (ppm): 6.41 (broad d, 1H, J=6.6 Hz), 5.40-5.34 (m, 4H), 4.72-4.69 (dt, 1H, J=3.6 Hz, J=3.7 Hz), 4.01-3.98 (ABX system, 1H, J=4.0 Hz, J=11.1 Hz), 3.96-3.93 (ABX system, 1H, J=3.4 Hz, J=11.2 Hz), 3.81 (s, 3H), 2.79 (t, 2H, J=7.0 Hz), 2.59 (broad s, 1H), 2.29 (m, 2H), 2.07 (m, 4H), 1.67 (m, 2H), 1.38-1.31 (m, 14H), 0.91 (t, 3H, J=6.9 Hz).

$^{13}$C {$^1$H} NMR (126 MHz, CDCl$_3$) δ (ppm): 173.68, 171.01, 130.23, 130.03, 128.06, 127.91, 63.71, 54.69, 52.75, 36.50, 31.51, 29.60, 29.33, 29.22, 29.18, 29.12, 27.19, 25.63, 25.52, 22.56, 14.04. One C is missing.

IR (neat cm$^{-1}$): v: 3363 (very broad), 3013, 2929, 2860, 1746, 1649, 1535, 1451, 1369, 1214, 1078, 982, 911, 718 (broad).

HRMS calcd for C$_{22}$H$_{39}$NO$_4$Na [M+Na]$^+$ 404.2771, found 404.2761. [α]$_D$=+21.7 (c 0.76, CHCl$_3$).

1.2 Synthesis of diethyl (9Z,12Z)-octadeca-9,12-dien-1-ylphosphonate, Called Hereafter "NKS-3"

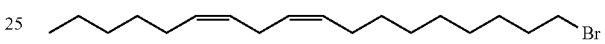

diethyl (9Z, 12Z)-octadeca-9,12-dien-1-ylphosphonate
Chemical Formula: C$_{22}$H$_{43}$O$_3$P
Molecular Weight: 386.55

This compound was prepared from linoleic acid via the alcohol (15mll-015) and the bromide (15 mll-016) described below. Both precursors are known in literature.

Step 1 (15 mll-015):

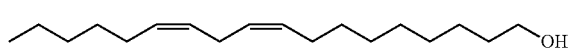

In a round bottom flask was suspended LiAlH$_4$ (0.18 g, 4.8 mmol) in THE (25 mL). A solution of linoleic acid (1.24 mL, 4.0 mmol) in THE (15 mL) was added dropwise at 0° C. The mixture was slowly warmed up to room temperature (20-25° C.) and stirred overnight. The mixture was quenched by addition of distilled water (2 mL) and 15% aqueous NaOH (5 mL). The mixture was diluted in EtOAc, transferred in a separating funnel then washed with brine. The organic phase was dried over MgSO$_4$ and concentrated. The product was purified by a column chromatography on SiO$_2$ (petroleum ether/ethyl acetate (5:1), R$_f$=0.80). $m_{pure}$=0.96 g. Aspect: colorless oil. Yield: 91%.

$^1$H NMR (500 MHz, CDCl$_3$) δ (ppm): 5.42-5.33 (m, 4H), 3.66 (t, 2H, J=6.6 Hz), 2.80 (m, 2H), 2.07 (m, 4H), 1.59 (m, 2H), 1.39-1.31 (m, 16H), 1.26 (broad s, 1H), 0.91 (t, 3H, J=7.0 Hz).

$^{13}$C {$^1$H} NMR (126 MHz, CDCl$_3$) δ (ppm): 130.20, 130.10, 128.01, 127.93, 63.07, 32.81, 31.52, 29.64, 29.48, 29.39, 29.34, 29.22, 27.20, 25.73, 25.63, 22.55, 14.03. One C is missing HRMS calcd for C$_{18}$H$_{34}$ONa [M+Na]$^+$ 289.2501, found 289.2503.

Step 2 (15 mll-016):

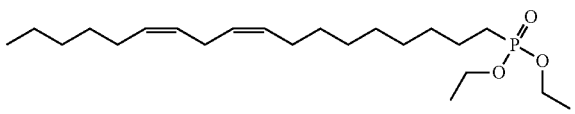

In a round bottom flask was introduced triphenylphosphine (1.90 g, 7.3 mmol), carbon tetrabromide (2.16 g, 6.5 mmol), and dichloromethane (DCM) (15 mL) was added at 0° C., the mixture is let stirred for 10 minutes (orange solution), then (9Z, 12Z)-octadecadien-1-ol (965.9 mg, 3.6 mmol) in DCM (10 mL) was transferred on the mixture via cannula at 0° C. A white precipitate was formed. The reaction mixture was let warm up overnight; then it was filtered over Celite® and concentrated under reduced pressure. The product was purified by a column chromatography on SiO$_2$ (petroleum ether/ethyl acetate (9:1), R$_f$=0.90). $m_{pure}$=0.96 g. Aspect: colorless oil. Yield: 80%.

$^1$H NMR (500 MHz, CDCl$_3$) δ (ppm): 5.42-5.34 (m, 4H), 3.43 (t, 2H, J=6.9 Hz), 2.79 (m, 2H), 2.07 (m, 4H), 1.88 (m, 2H), 1.45 (m, 2H), 1.39-1.31 (m, 14H), 0.92 (t, 3H, J=7.0 Hz)

$^{13}$C {$^1$H} NMR (126 MHz, CDCl$_3$) δ (ppm): 130.20, 130.10, 128.01, 63.07, 32.81, 31.52, 29.64, 29.48, 29.39, 29.34, 29.22, 27.20, 25.73, 25.63, 22.55, 14.03. One C is missing.

HRMS calcd for C$_{18}$H$_{32}$Br [M-H]$^+$ 327.1681, found 327.1682.

Step 3:

In a Schlenk were introduced diethyl phosphite (0.34 mL, 2.6 mmol) and THE (2 mL). The mixture was cooled to 0° C. and sodium bis(trimethylsilyl)amide (NaHMDS) 2M (1.5 mL, 3.0 mmol) was added. The mixture was stirred at room temperature (20-25° C.) for half an hour. Then the reaction was cooled to 0° C. and (6Z, 9Z)-18-bromooctadeca-6,9-diene (0.35 g, 1.07 mmol) in THE (2 mL) was transferred on the reaction mixture via cannula. After 30 minutes, the mixture was stirred overnight at 25° C. The reaction medium was concentrated under reduced pressure, and purified by column chromatography on SiO$_2$ (petroleum ether/ethyl acetate (1:4), R$_f$=0.50). $m_{pure}$=0.35 g. Aspect slightly yellow oil. Yield: 85%.

$^1$H NMR (500 MHz, CD$_2$Cl$_2$) δ (ppm): 5.44-5.34 (m, 4H), 4.12-4.03 (m, 4H), 2.82 (m, 2H), 2.09 (m, 4H), 1.74-1.68 (m, 2H), 1.62-1.57 (m, 2H), 1.39-1.32 (m, 22H), 0.93 (t, 3H, J=7.0 Hz)

$^{13}$C {$^1$H} NMR (126 MHz, CD$_2$C$_2$) δ (ppm): 130.08, 130.02, 127.92, 127.87, 61.19 (d, J=6.3 Hz), 31.51, 30.62, 30.49, 29.63, 29.33, 29.24 (d, J=6.3 Hz), 29.05, 27.15 (d, J=2.8 Hz), 26.11, 25.55, 25.00, 22.53, 22.40 (d, J=5.3 Hz), 16.26 (d, J=5.3 Hz), 13.79.

$^{31}$P NMR (203 MHz, CDCl$_3$) δ (ppm): +32.05 (s).

IR (neat cm$^{-1}$): v: 3009, 2926, 2855, 1463, 1392, 1245, 1164, 1097, 1056, 1028, 954, 785, 722.

HRMS calcd for C$_{22}$H$_{44}$O$_3$P [M+H]$^+$ 387.3023, found 387.3019.

1.3 Synthesis of (9Z,12Z)-(3-methyloxetan-3-yl) methyl octadeca-9,12-dienoate, Called Hereafter "NKS-5"

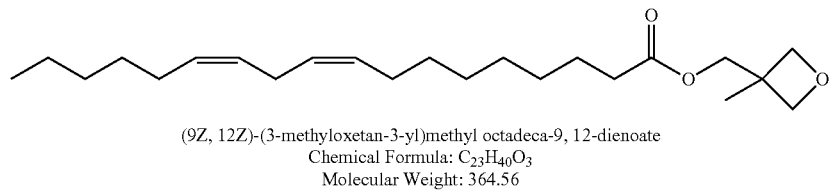 [SMILES: CCCCC/C=C\C/C=C\CCCCCCCC(=O)OCC1(C)COC1]

(9Z, 12Z)-(3-methyloxetan-3-yl)methyl octadeca-9, 12-dienoate
Chemical Formula: C$_{23}$H$_{40}$O$_3$
Molecular Weight: 364.56

In a round bottom flask were introduced linoleic acid (1.24 mL, 4.0 mmol) and dichloromethane (8 mL) under inert atmosphere. The mixture was cooled to 0° C. and oxalyl chloride (0.38 mL, 4.4 mmol) was introduced dropwise. Then the catalytic quantity of dimethylformamide (DMF) (0.03 mL) was added. The reaction mixture was stirred for 1 h at 0° C. and for 2 h at room temperature (20-25° C.). Solvents and oxalyl chloride were removed under reduced pressure and the product was directly engaged in the following step (aspect: colorless oil with slight precipitate).

A solution of 3-methyl-3-oxetane methanol (0.52 mL, 5.2 mmol), triethylamine (0.73 mL, 5.2 mmol) in THF (20 mL) was prepared in a round bottom flask under inert atmosphere. The mixture was cooled to 0° C. and freshly prepared linoleoyl chloride (1.16 g, 4.0 mmol) in THF (20 mL) was added via cannula. After stirring for 1 h at RT, the mixture was worked up by addition of distilled water (6 mL). The product was extracted with ethyl acetate (3×15 mL), dried over MgSO$_4$ and purified by column chromatography on SiO$_2$ (petroleum ether/ethyl acetate (5:1), R$_f$=0.70). m$_{pure}$=0.85 g. Aspect: colorless oil. Yield: 80%.

$^1$H NMR (500 MHz, CDCl$_3$) δ (ppm): 5.39-5.36 (m, 4H), 4.54 (d, 2H, J=6.0 Hz), 4.40 (d, 2H, J=6.0 Hz), 4.18 (s, 2H), 2.79 (t, 2H, J=6.9 Hz), 2.37 (t, 2H, J=7.5 Hz), 2.07 (q, 4H, J=6.8 Hz), 1.66 (m, 2H, J=7.2 Hz), 1.38-1.31 (m, 17H), 0.91 (t, 3H, J=6.9 Hz).

$^{13}$C {$^1$H} NMR (126 MHz, CDCl$_3$) δ (ppm): 174.00, 130.36, 130.15, 128.22, 128.05, 79.74, 68.60, 39.26, 34.36, 31.67, 29.73, 29.48, 29.29, 29.26, 29.24, 27.34, 27.32, 25.78, 25.12, 22.70, 21.34, 14.19. One C is missing. IR (neat cm$^{-1}$): v: 3010 (small), 2928 (broad), 2857 (broad), 1739, 1460, 1378, 1351, 1240, 1163 (broad), 1099, 984, 942, 834, 723 (broad). HRMS calcd for C$_{23}$H$_{41}$O$_3$ [M+H]$^+$ 365.3050, found 365.3043.

1.4 Synthesis of methyl (S)-2-((8Z,11Z)-heptadeca-8,11-dien-1-yl)-4,5-dihydrooxazole-4-carboxylate, Called Hereafter "NKS-6"

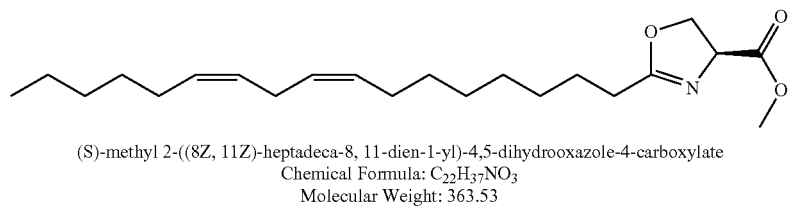 [SMILES: CCCCC/C=C\C/C=C\CCCCCCCC1=N[C@H](C(=O)OC)CO1]

(S)-methyl 2-((8Z, 11Z)-heptadeca-8, 11-dien-1-yl)-4,5-dihydrooxazole-4-carboxylate
Chemical Formula: C$_{22}$H$_{37}$NO$_3$
Molecular Weight: 363.53

In a Schlenk was introduced methyl (S)-3-hydroxy-2-((9Z,12Z)-octadeca-9,12-dienamido)propanoate (0.19 g, 0.5 mmol), DCM (1 mL) and then (iPr)$_2$NEt (0.19 mL, 1.1 mmol). After 30 min, the mixture was cooled to 0° C. and Deoxofluor (0.24 mL, 1.1 mmol) was added dropwise. After 16 h, the crude mixture was directly engaged on $SiO_2$ gel chromatography for purification (petroleum ether/ethyl acetate (1:1), $R_f$=0.75). $m_{pure}$=0.17 g. Aspect: colorless oil. Yield: 92%.

$^1$H NMR (600 MHz, $CDCl_3$) δ (ppm):

Step-1 (15mll-052): 5.42-5.34 (m, 4H), 4.76-4.73 (m, 1H), 4.50 (1H, J=7.8 Hz), 4.41 (m, 1H), 3.81 (s, 3H), 2.80 (m, 2H), 2.35 (m, 2H), 2.08 (m, 4H), 1.67 (m, 2H), 1.39-1.31 (m, 14H), 0.92 (t, 3H, J=6.7 Hz).

$^{13}$C {$^1$H} NMR (126 MHz, $CDCl_3$) δ (ppm):

Step-2 (15mll-030): 171.67, 171.12, 130.20, 130.04, 128.04, 127.91, 69.32, 67.92, 52.56, 31.51, 29.57, 29.32, 29.08, 27.95, 27.19, 25.87, 25.62, 22.54, 14.02. 3 C are missing IR (neat $cm^{-1}$): v: 3009, 2925, 2854, 1743, 1660, 1459, 1436, 1362, 1270, 1204, 1177, 1060, 1037, 986, 955, 915, 723.

HRMS calcd for $C_{22}H_{38}NO_3$ $[M+H]^+$ 364.2846, found 364.2842. $[α]_D$=+33.5 (c 1.7, EtOAc).

1.5 Synthesis of (9Z,12Z)-(tetrahydrofuran-2-yl)methyl octadeca-9,12-dienoate, Called Hereafter "1x"

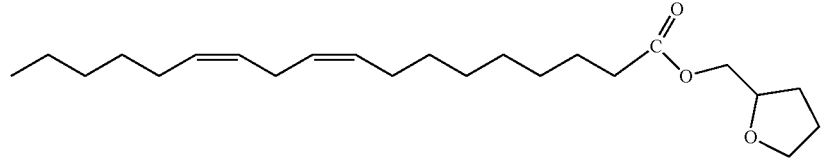

(9Z,12Z)-(tetrahydrofuran-2-yl)methyl octadeca-9,12-dieneoate
Chemical Formula: $C_{23}H_{40}O_3$
Molecular Weight: 364.57

17FM024: In a round bottom flask were introduced linoleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 μL) was added. The reaction mixture was stirred for 1 h at 0° C. and for 2 h at room temperature. Solvents and oxalyl chloride were removed under reduced pressure and the product was directly engaged in the following step. Aspect: yellow oil with slight precipitate.

A solution of tetrahydrofurfuryl alcohol (0.14 mL, 1.42 mmol), triethylamine (0.2 mL, 1.42 mmol) in THF (4 mL) was prepared in a round bottom flask under inert atmosphere. The mixture was cooled to 0° C. and freshly prepared linoleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over $MgSO_4$ and purified by column chromatography on $SiO_2$ (petroleum ether/ethyl acetate (5:1), $R_f$=0.70). $m_{pure}$=0.23 g. Aspect: colorless oil. Yield: 88%.

$^1$H NMR (500 MHz, $CDCl_3$) δ (ppm): 5.41-5.30 (m, 4H), 4.16 (dd, 1H, J=3.6 Hz, J=11.2 Hz), 4.11 (ddd, 1H, J=3.6 Hz, J=6.9 Hz, J=14.0 Hz), 3.99 (dd, 1H, J=6.7 Hz, J=11.2 Hz), 3.89 (dd, 1H, J=6.7 Hz, J=8.2 Hz), 3.82-3.77 (m, 1H), 2.77 (t, 2H, J=6.6 Hz), 2.34 (t, 2H, J=7.6 Hz), 2.07-1.86 (m, 6H), 1.65-1.56 (m, 4H), 1.38-1.25 (m, 14H), 0.89 (t, 3H, J=6.9 Hz).

$^{13}$C {$^1$H} NMR (126 MHz, $CDCl_3$) δ (ppm): 173.80, 130.20, 130.04, 128.02, 127.90, 76.55, 68.43, 66.31, 34.20, 31.51, 29.59, 29.33, 29.15, 29.10 (2×), 27.99, 27.19 (2×), 25.65, 25.62, 24.91, 22.56, 14.06.

IR (neat $cm^{-1}$): v: 3008, 2924, 2854, 1737, 1458, 1362, 1239, 1169, 1082, 1023, 991, 916, 722.

1.6 Synthesis of (9Z,12Z)-(tetrahydrofuran-3-yl)methyl octadeca-9,12-dienoate, Called Hereafter "1a"

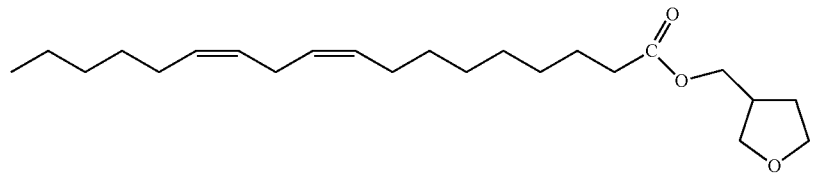

(9Z,12Z)-(tetrahydrofuran-3-yl)methyl octadeca-9,1-dieneoate
Chemical Formula: $C_{23}H_{40}O_3$
Molecular Weight: 364.57

17FM090: In a round bottom flask were introduced linoleic acid (220 mg, 0.78 mmol) and dichloromethane (2 mL) under inert atmosphere. The mixture was cooled to 0° C. and oxalyl chloride (0.08 mL, 0.86 mmol) was introduced dropwise. Then the catalytic quantity of DMF (5.5 µL) was added. The reaction mixture was stirred for 1 h at 0° C. and for 2 h at room temperature. Solvents and oxalyl chloride were removed under reduced pressure and the product was directly engaged in the following step. Aspect: yellow oil with slight precipitate.

A solution of tetrahydro-3-furanmethanol (0.14 mL, 1.42 mmol), triethylamine (0.2 mL, 1.42 mmol) in THF (4 mL) was prepared in a round bottom flask under inert atmosphere. The mixture was cooled to 0° C. and freshly prepared oleoyl chloride (233 mg, 0.78 mmol) in THF (4 mL) was added via cannula. After stirring for overnight at RT, the mixture was worked up by addition of distilled water (6 mL). The product was extracted with ethyl acetate (3×15 mL), dried over $MgSO_4$ and purified by column chromatography on $SiO_2$ (petroleum ether/ethyl acetate (5:1), $R_f$=0.70). $m_{pure}$=234.1 mg. Aspect: colorless oil. Yield: 82%.

$^1$H NMR (500 MHz, $CDCl_3$) δ (ppm): 5.46-5.25 (m, 4H), 4.08 (dd, 1H, J=6.5 Hz, J=10.9 Hz), 3.97 (dd, 1H, J=8.0 Hz, J=10.9 Hz), 3.88-3.81 (m, 2H), 3.75 (dt, 1H, J=7.2 Hz, J=8.5 Hz), 3.56 (dd, 1H, J=5.6 Hz, J=8.8 Hz), 2.80-2.72 (m, 2H), 2.80-2.52 (m, 1H), 2.30 (t, 2H, J=7.5 Hz), 2.09-1.98 (m, 5H), 1.67-1.57 (m, 3H), 1.41-1.24 (m, 14H), 0.88 (t, 3H, J=6.9 Hz).

$^{13}$C {$^1$H} NMR (126 MHz, $CDCl_3$) δ (ppm): 173.74, 130.20, 130.00, 128.04, 127.88, 70.53, 67.70, 65.65, 38.26, 34.24, 31.50, 29.57, 29.32, 29.13, 29.09, 29.08, 28.94, 27.18, 27.16, 25.61, 24.94, 22.55, 14.04.

IR (neat cm$^{-1}$): v: 3009, 2925, 2854, 1738, 1456, 1394, 1357, 1240, 1167, 1079, 1011, 914, 723, 600.

1.7 Synthesis of (9Z,12Z)-(oxetan-3-yl)methyl octadeca-9,12-dienoate, Called Hereafter "1b"

In a round bottom flask were introduced linoleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 µL) was added. The reaction mixture was stirred for 1 h at 0° C. and for 2 h at room temperature. Solvents and oxalyl chloride were removed under reduced pressure and the product was directly engaged in the following step. Aspect: yellow oil with slight precipitate.

A solution of 3-oxetane alcohol (0.12 mL, 1.42 mmol), triethylamine (0.2 mL, 1.42 mmol) in THF (4 mL) was prepared in a round bottom flask under inert atmosphere. The mixture was cooled to 0° C. and freshly prepared linoleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over $MgSO_4$ and purified by column chromatography on $SiO_2$ (petroleum ether/ethyl acetate (5:1), $R_f$=0.73). $m_{pure}$=0.23 g. Aspect: colorless oil. Yield: 94%.

$^1$H NMR (500 MHz, $CDCl_3$) δ (ppm): 5.41-5.30 (m, 4H), 4.81-4.78 (m, 2H), 4.47 (dt, 2H, J=2.1 Hz, J=6.2 Hz), 4.30 (dd, 2H, J=1.9 Hz, J=6.7 Hz), 3.33-3.24 (m, 1H), 2.77 (t, 2H, J=6.6 Hz), 2.32 (dt, 2H, J=1.8 Hz, J=7.7 Hz), 2.04 (q, 4H, J=6.9 Hz), 1.65-1.59 (m, 2H), 1.38-1.27 (m, 14H), 0.89 (dt, 3H, J=1.8 Hz, J=6.9 Hz).

$^{13}$C {$^1$H} NMR (126 MHz, $CDCl_3$) δ (ppm): 173.80, 130.21, 129.99, 128.05, 127.87, 74.10 (2×), 64.99, 34.16, 34.09, 31.51, 29.57, 29.33, 29.13, 29.08 (2×), 27.19, 27.17, 25.62, 24.92, 22.53, 14.06.

IR (neat cm$^{-1}$): v: 3008, 2925, 2855, 1737, 1461, 1362, 1239, 1163, 1051, 982, 853, 723.

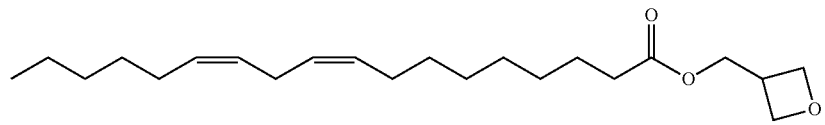

(9Z,12Z)-(oxetan-3-yl)methyl octadeca-9,12-dienoate
Chemical Formula: $C_{22}H_{38}O_3$
Molecular Weight: 350.54

1.8 Synthesis of (9Z,12Z)-(oxyran-3-yl)methyl octadeca-9,12-dienoate, Called Hereafter "1c"

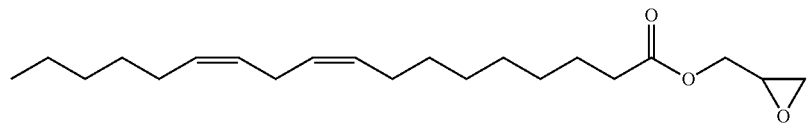

(9Z,12Z)-(oxiran-3-yl)methyl octadeca-9,12-dienoate
Chemical Formula: $C_{21}H_{36}O_3$
Molecular Weight: 336.27

17FM33: In a round bottom flask were introduced linoleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 μL) was added. The reaction mixture was stirred for 1 h at 0° C. and for 2 h at room temperature. Solvents and oxalyl chloride were removed under reduced pressure and the product was directly engaged in the following step. Aspect: yellow oil with slight precipitate.

A solution of glycidol (105.2 mg, 1.42 mmol), triethylamine (0.2 mL, 1.42 mmol) in THF (4 mL) was prepared in a round bottom flask under inert atmosphere. The mixture was cooled to 0° C. and freshly prepared linoleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over $MgSO_4$ and purified by column chromatography on $SiO_2$ (petroleum ether/ethyl acetate (5:1), $R_f$=0.73). $m_{pure}$=0.21 g. Aspect: colorless oil. Yield: 91%.

$^1$H NMR (500 MHz, $CDCl_3$) δ (ppm): 5.41-5.30 (m, 4H), 4.41 (dd, 1H, J=3.1 Hz, J=12.3 Hz), 3.91 (dd, 1H, J=6.3 Hz, J=12.3 Hz), 3.20 (ddd, 1H, J=2.9 Hz, J=4.1 Hz, J=9.4 Hz), 2.84 (t, 1H, J=4.5 Hz), 2.77 (t, 2H, J=6.6 Hz), 2.64 (dd, 1H, J=2.6 Hz, J=4.9 Hz), 2.35 (t, 2H, J=7.6 Hz), 2.04 (q, 4H, J=6.8 Hz), 1.66-1.60 (m, 2H), 1.38-1.25 (m, 14H), 0.89 (t, 3H, J=6.9 Hz).

$^{13}$C $\{^1H\}$ NMR (126 MHz, $CDCl_3$) δ (ppm): 173.50, 130.21, 130.02, 128.04, 127.89, 64.74, 49.38, 44.66, 34.05, 31.52, 29.58, 29.34, 29.14, 29.08 (2×), 27.19, 27.18, 25.62, 24.85, 22.56, 14.06.

IR (neat cm$^{-1}$): v: 3008, 2924, 2854, 1739, 1458, 1374, 1245, 1171, 1013, 910, 853, 722.

1.9 Synthesis of (9Z,12Z)-(2,2,5-trimethyl-1,3-dioxan-5-yl)methyl octadeca-9,12-dienoate, Called Hereafter "1d"

This compound was prepared by reaction of linoleic acid and 2,2,5-trimethyl-1,3-dioxane-5-methanol (17FM025), known in literature and prepared as described below.

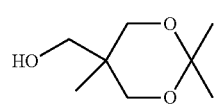

17FM025: In a round bottom flask were introduced tris(hydroxymethyl)ethane (2 g, 16.7 mmol) and a catalytic quantity of PTSA (2 mg) in acetone (20 mL) under inert atmosphere. The mixture was stirred at room temperature for 2 days. The reaction was neutralized with 50 mg of $K_2CO_3$, filtrated and evaporated to give the desired product with 96% of purity. $m_{pure}$=2.64 g. Aspect: colorless oil. Yield: 98%.

$^1$H NMR (500 MHz, DMSO) (ppm): 4.57 (t, 1H, J=5.4 Hz), 3.57 (AB system, 2H, J=11.7 Hz), 3.44 (AB system, 2H, J=11.7 Hz), 3.35 (d, 1H, J=5.3 Hz), 1.33 (s, 3H), 1.27 (s, 3H), 0.75 (s, 3H).

$^{13}$C $\{^1H\}$ NMR (126 MHz, DMSO) δ (ppm): 96.92, 65.34, 34.22, 25.80, 21.57, 17.61.

Compound 1d: In a round bottom flask were introduced linoleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 μL) was added. The reaction mixture was stirred for 1 h at 0° C. and for 2 h at room temperature. Solvents and oxalyl chloride were removed under reduced pressure and the product was directly engaged in the following step. Aspect: yellow oil with slight precipitate.

A solution of 2,2,5-trimethyl-1,3-dioxane-5-methanol (228 mg, 1.42 mmol), triethylamine (0.2 mL, 1.42 mmol) in THF (4 mL) was prepared in a round bottom flask under inert atmosphere. The mixture was cooled to 0° C. and freshly prepared linoleoyl chloride (212 mg, 0.7 mmol) in THF (4 mL) was added via cannula. After stirring for overnight at RT, the mixture was worked up by addition of distilled water (6 mL). The product was extracted with ethyl

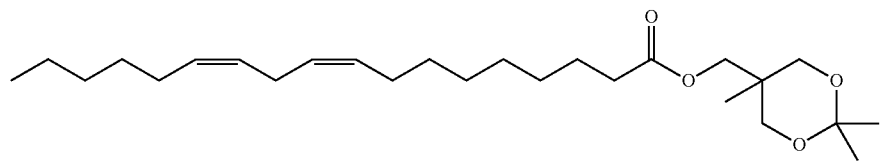

(9Z,12Z)-(2,2,5-trimethyl-1,3-dioxan-5-yl)methyl ocatadeca-9,12-dienoate
Chemical Formula: $C_{26}H_{46}O_4$
Molecular Weight: 422.65 acetate (3×15 mL), dried over MgSO$_4$ and purified by column chromatography on SiO$_2$ (petroleum ether/ethyl acetate (5:1), R$_f$=0.73). m$_{pure}$=213.6 mg. Aspect: colorless oil. Yield: 91%.

$^1$H NMR (500 MHz, CDCl$_3$) δ (ppm): 5.41-5.30 (m, 4H), 4.15 (s, 2H), 3.60 (AB system, 2H, J=12.0 Hz), 3.53 (AB system, 2H, J=12.0 Hz), 2.77 (t, 2H, J=6.6 Hz), 2.34 (t, 2H, J=7.6 Hz), 2.05 (q, 4H, J=7.0 Hz), 1.66-1.60 (m, 2H), 1.44 (s, 3H), 1.40 (s, 3H), 1.37-1.25 (m, 14H), 0.89 (t, 3H, J=6.9 Hz), 0.85 (s, 3H).

$^{13}$C {$^1$H} NMR (126 MHz, CDCl$_3$) δ (ppm): 173.80, 130.24, 130.06, 128.07, 127.92, 98.07, 66.65, 66.33 (2×), 34.33, 33.55, 31.55, 29.62, 29.37, 29.20, 29.17, 29.14, 27.23 (2×), 26.82, 25.66, 24.98, 22.60, 20.56, 17.83, 14.10.

IR (neat cm$^{-1}$): v: 2992, 2925, 2855, 1737, 1456, 1395, 1373, 1343, 1264, 1246, 1226, 1205, 1186, 1155, 1089, 1042, 1024, 933, 913, 829, 728.

1.10 Synthesis of (9Z,12Z)-(2-oxopropyl)-octadeca-9,12-dienoate, Called Hereafter "1e"

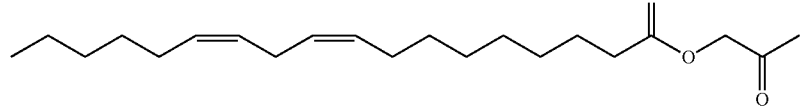

((9Z,12Z)-oxopropyl ocatadeca-9,12-dienoate
Chemical Formula: C$_{21}$H$_{36}$O$_3$
Molecular Weight: 336.24

In a round bottom flask were introduced linoleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 µL) was added. The reaction mixture was stirred for 1 h at 0° C. and for 2 h at room temperature. Solvents and oxalyl chloride were removed under reduced pressure and the product was directly engaged in the following step. Aspect: yellow oil with slight precipitate.

A solution of hydoxyacetone (0.2 mL, 1.42 mmol), triethylamine (0.2 mL, 1.42 mmol) in THF (4 mL) was prepared in a round bottom flask under inert atmosphere. The mixture was cooled to 0° C. and freshly prepared linoleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over MgSO$_4$ and purified by column chromatography on SiO$_2$ (petroleum ether/ethyl acetate (5:1.5), R$_f$=0.6). m$_{pure}$=151.4 mg. Aspect: colorless oil. Yield: 64%.

$^1$H NMR (500 MHz, CDCl$_3$) δ (ppm): 5.41-5.30 (m, 4H), 4.64 (s, 2H), 2.77 (t, 2H, J=6.7 Hz), 2.42 (t, 2H, J=7.6 Hz), 2.16 (s, 3H), 2.05 (q, 4H, J=6.8 Hz), 1.70-1.64 (m, 2H), 1.38-1.25 (m, 14H), 0.89 (t, 3H, J=6.9 Hz).

$^{13}$C {$^1$H} NMR (126 MHz, CDCl$_3$) δ (ppm): 201.69, 173.03, 130.21, 130.03, 128.03, 127.89, 68.14, 33.80, 31.52, 29.59, 29.34, 29.15, 29.09, 29.04, 27.20, 27.18, 26.08, 25.62, 24.82, 22.57, 14.06.

IR (neat cm$^{-1}$): v: 3008, 2924, 2854, 1734, 1460, 1417, 1372, 1270, 1154, 1099, 966, 909, 722.

2. Biological Properties

2.1 Materials and Methods a—Animals

Eight weeks old, male mice (C57Bl/6 black) were purchased from the Janvier Elevage (Le Mans) and used for the experiments.

b—Isolation of taste bud cells

The experimental protocol for isolation/purification of taste cells from fungiform papillae was approved by the Regional Ethical Committee (protocol number: A0508).

The technique to isolate taste bud cells from mouse fungiform papillae has been described in the publication of El-Yassimi A, Hichami A, Besnard P, Khan N A. "Linoleic acid induces calcium signaling, Src kinase phosphorylation, and neurotransmitter release in mouse CD36-positive gustatory cells"—*J Biol Chem.* 2008 May 9; 283(19):12949-59.

Briefly, lingual epithelium was separated by enzymatic dissociation which contained the following: elastase and dispase mixture, 2 mg/ml each, in Tyrode's buffer (120 mM NaCl; 5 mM KCl; 10 mM HEPES ((4-(2-hydroxyethyl)-1-piperazineethanesulfonic acid); 1 mM CaCl$_2$; 1 mM MgCl$_2$; 10 mM glucose; 10 mM Na pyruvate, pH 7.4). The taste bud cells were isolated by incubating lingual epithelium in RPMI 1640 medium containing 2 mM EDTA, 1.2 mg/ml elastase, 0.6 mg/ml collagenase (type 1), and 0.6 mg/ml trypsin inhibitor at 37° C. for 10 minutes, followed by centrifugation (600 g, 10 minutes). The cell populations, after separation, were suspended in fresh RPMI 1640 medium containing 10% fetal calf serum, 200 U/ml penicillin, and 0.2 mg/ml streptomycin, seeded onto a Poly-D-Lysine-coated dishes, and cultured for 24 hours. At the end of this period, the cells were used for the experiments or stained with trypan blue to assess their viability.

c—"Ca$^{2+}$ Signaling" for Showing the Interaction with CD36 and/or GPR120 Fat Taste Receptors Ca$^{2+}$ is the key second messenger in mammalian cells. It regulates a variety of cellular functions. Phospholipase C (PLC) is responsible for the hydrolysis of phosphatidylinositol-4,5-bisphosphate (PIP$_2$), generating two second messengers, i.e., inositol-1, 4,5-triphosphate (hereafter IP$_3$) and diacylglycerol (DAG). The PLCβ subfamily is of particular interest, given its prominent role in neuronal and Taste Bud Cells (TBC) signaling, and its regulation by G Protein-Coupled Receptors (hereafter GPCR). IP$_3$ is freely diffusible and binds to IP$_3$-specific receptors, leading to the release of Ca$^{2+}$ from the endoplasmic reticulum (ER) which represents the intracellular Ca$^{2+}$ pool.

As regards taste perception, an increase in [Ca$^{2+}$]i has been considered as one of the earliest mechanisms, involved in the transfer of taste message from the tongue to the brain. The publication of El-Yassimi et al. mentioned above shows that CD36 and GPR120 (Ozdener M H et al. "CD36- and GPR120-mediated Ca$^{2+}$ signaling in human taste bud cells mediates differential responses to fatty acids and is altered in obese mice"—*Gastroenterology* 2014, April, 146(4), 995-1005) in human and taste bud cells are coupled to an increase in free [Ca$^{2+}$]i during their activation by fatty acids like linoleic acid. In mouse taste bud cells, the linoleic acid via CD36 induced the phosphorylation of src-kinases, (Fyn$^{59}$ and Yes$^{62}$) and regulated the increases in [Ca$^{2+}$]i by opening of calcium channels whose opening was controlled by stromal interaction molecule-1, STIM-1 (publication Dramane G et al. "STIM1 regulates calcium signaling in taste bud cells and preference for fat in mice", *J. Clin. Invest.* 2012, June, 122(6), 2267-82).

Thus, it can be stated that Ca$^{2+}$ signaling (under the control of STIM1), plays a key role in the signaling of fat taste transduction in mice.

Therefore, the mobilization of intracellular calcium in response to the linoleic acid derivatives of the invention was studied by the Applicant.

d—Method of Measurement of the Ca$^{2+}$ Signaling in Mouse Bud Cells

The mouse taste bud cells were seeded in 24-well plates (with glass bottom), containing poly-D-lysine for better adhesion to the surface. After 24 h, taste cells were incubated for 45 minutes with a fluorescent probe, Fura-2/AM (1 μM) in calcium buffer (110 mM NaCl, 5.4 mM, KCl, 25 mM, NaHCO$_3$, 0.8 mM, MgCl$_2$, 0.4 mM, KH$_2$PO$_4$, 20 mM, Hepes-Na, 0.33 mM, NaHPO$_4$, 1.2 mM, CaCl$_2$, pH 7.4). Then, the cells are washed with phosphate buffer saline (PBS) and taken up in calcium buffer.

The changes in intracellular Ca$^{2+}$ (F$_{340}$/F$_{380}$) were monitored under a Nikon microscope (TiU) by using an S Fluor 40× oil immersion objective.

Especially, the increases in [Ca$^{2+}$]i were measured as follows: the mice taste bud cells were cultured on Willico-Dish wells with a glass bottom and loaded with a fluorescent probe, Fura-2/AM. The changes in intracellular Ca$^{2+}$ (F$_{340}$/F$_{380}$) were monitored under the Nikon microscope (TiU) by using S-fluor 40× oil immersion objective. The planes were taken at Z intervals of 0.3 μm, and NIS-Elements software was used to deconvolve the images. The microscope was equipped with EM-CCD (Lucas) camera for real time recording of 16-bit digital images. The dual excitation fluorescence imaging system was used for studies of individual cells. The changes in intracellular Ca$^2$ were expressed as ΔRatio, which was calculated as the difference between the peak F$_{340}$/F$_{380}$ ratio. The data were summarized from the large number of individual cells (20-40 cells in a single run, with 3-9 identical experiments done in at least three cell preparations). The results were analyzed with the NIS-elements software, the variation in [Ca$^{2+}$]i is expressed as Δ ratio (F$_{340}$/F$_{380}$ which was calculated with the difference of spectra at two wavelengths, i.e., 340 nm and 380 nm.

CD36: in order to assess if the linoleic acid derivatives according to the invention exert their actions via CD36, sulfo-N-succinimidyl oleate (SSO) was used. SSO is a CD36 inhibitor/blocker/antagonist.

Experiments were performed in the presence or absence of SSO with respect to calcium signaling to verify whether our analogs act well via this lipid receptor. Especially, for this assay, NKS-3, NKS-5 and linoleic acid (control) were tested.

GPR120: in order to assess if the linoleic acid derivatives according to the invention exert their actions via GPR120, AH7614 was used. This commercially available compound is a GPR120 antagonist.

Experiments were performed in the presence or absence of SSO and/or AH7614 with respect to calcium signaling to verify whether our analogs act well via this lipid receptor.

Especially, for this assay, NKS-3, NKS-5 and linoleic acid (control) were tested.

2.1 Results a—Action on CD36 Fat Taste Receptor (FIG. 1)

FIG. 1A shows that LA, the control molecule, in mice taste bud cells, induces a huge increase in [Ca$^{2+}$]i via CD36. This phenomenon is suppressed by the presence of SSO.

Figure 1B:
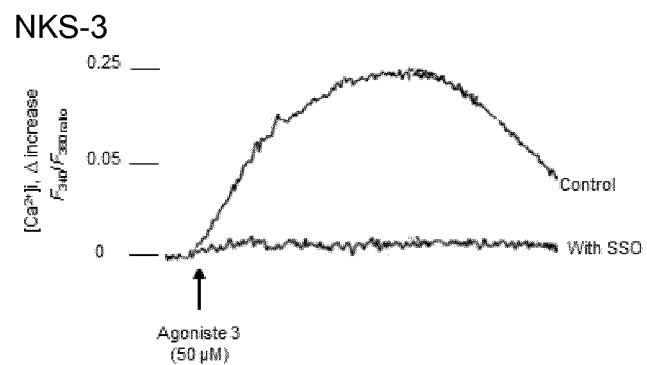
Figure 1C:
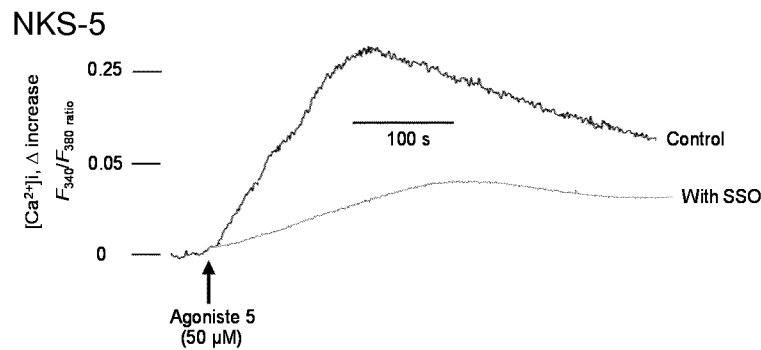

FIG. 1B proves that NKS-3 is a complete CD36 agonist as its action was completely suppressed by SSO. The NKS-5 appears to be a partial agonist because its action on the increases in [Ca$^{2+}$]i was curtailed, but not completely suppressed, by SSO (FIG. 1C).

Figure 2:
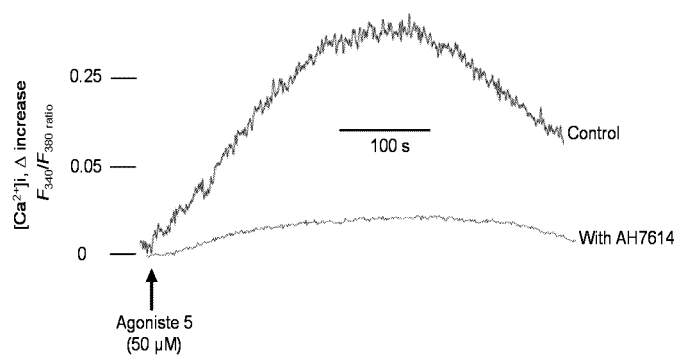
FIG. 2: Effect of GPR120 inhibitor (AH7614 that is a commercially available known GPR120 antagonist) at 20 µM on the increase in $[Ca^{2+}]i$ by the linoleic acid derivative NKS-5 according to the invention (at 50 µM) in mouse taste bud cells.
Figure 3A:
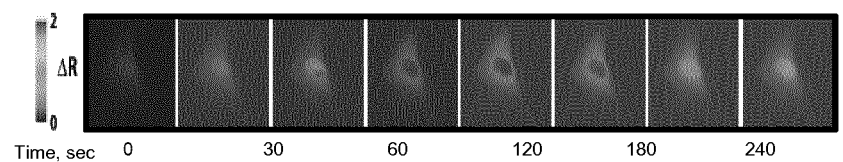
FIG. 3A shows the increases in $[Ca^{2+}]i$, expressed as changes in pseudocolour images, as function of time in seconds in freshly isolated taste bud cells where 50 µM of the linoleic acid derivative NKS-3, according to the invention, was added.
Figure 3B:
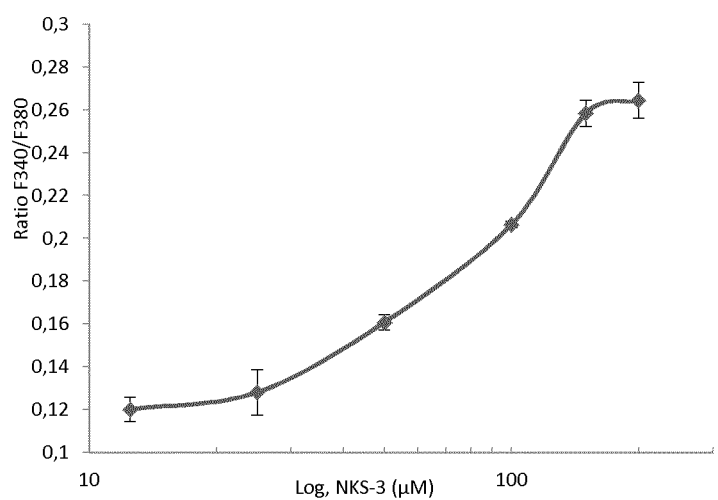
FIG. 3B is a graphic which shows the dose-dependent increases in $[Ca^{2+}]i$ expressed as A ratio (ratio of $F_{340}/F_{390}$) in accordance with the increase of the NKS-3 concentration from 0 to 200 µM expressed in Log (the values are means±SD of n=6 assays).

In addition, FIG. 3A shows that NKS-3 induced in mouse taste bud cells an increase in [Ca$^{2+}$]i which is very rapid. Especially, this compound induces the increases in [Ca$^{2+}$]i in a dose-dependent manner with an EC$_{50}$ value of 25±0.01 μM (FIG. 3B).

b—Action on GPR120 Fat Taste Receptor (FIG. 2)

As it is shown by FIG. 2, NKS-5 according to the invention also acts via GPR120 since AH7614 abolished partially its action on the increase in [Ca$^{2+}$]i in mouse gustatory cells. Indeed, FIG. 2 shows that the response of NKS-5 was significantly curtailed, but not suppressed, by AH7614. The results at 25 μM and 50 μM of NKS-3 are identical.

Figure 4A:
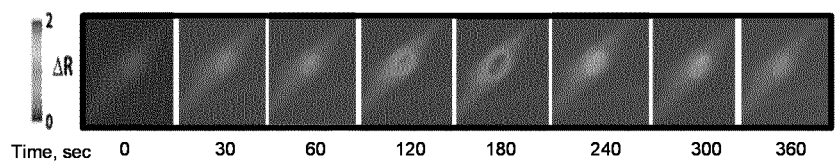
FIG. 4A shows the increases in $[Ca^{2+}]i$ expressed as pseudocolour images, as function of time in seconds in freshly isolated taste bud cells where 50 µM of the linoleic acid derivative NKS-5 according to the invention was added.
Figure 4B:
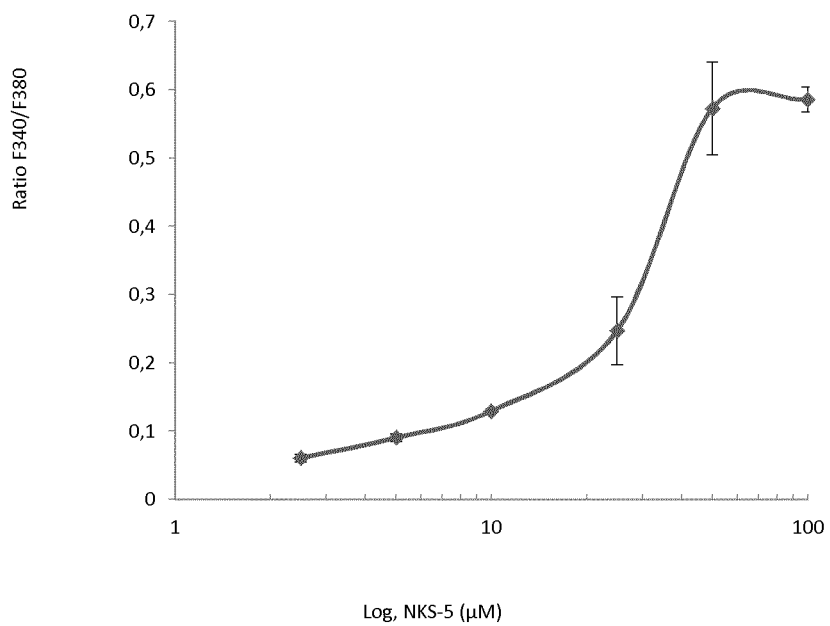
FIG. 4B is a graphic which also shows the $[Ca^{2+}]i$ variation expressed as A ratio (ratio of $F_{340}/F_{380}$ in accordance with the increase of the NKS-5 concentration from 0 to 200 µM expressed in Log (the values are means±SD of n=6 assays)

Similar to NKS-3, the NKS-5-induced increases in [Ca$^2$]i is also very rapid (FIG. 4A) in mouse taste bud cells. This compound according to the invention induces in particular the increases in a dose-dependent manner with an EC$_{50}$ value of 30±0.01 μM (FIG. 4B).

3. Fat-Like Taste Perception

3.1 Materials and Methods a—Animals

Eight weeks old, male mice (C57Bl/6 black) were purchased from the Janvier Elevage (Le Mans) and used for these experiments.

b—Methods of Two-Bottle Preference Test

The mice are placed individually in cages in a controlled environment (humidity and constant temperature) and have free access to a standard diet. 6 hours before the tests, the mice are deprived of water.

During the behavioral experiments, the mice were offered two bottles simultaneously for 12 hours (night period).

The mice are subjected to a choice between the "control" solution and the experimental solution.

Figure 5:
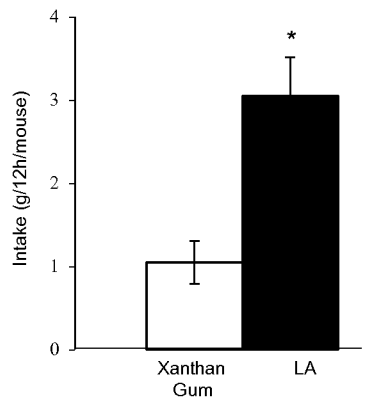
FIG. 5: is a histogram showing the results of a two-bottle preference test: the tested mice were subjected to two bottles, one containing xanthan gum (white column) and the other one containing xanthan gum and linoleic acid (0.2%, v/v) (black column)—the asterisk shows the significant intake difference (g/12 h/mouse) as compared to the control solution (p<0.001) as per statistical students t-test of significance.
Figure 6A:
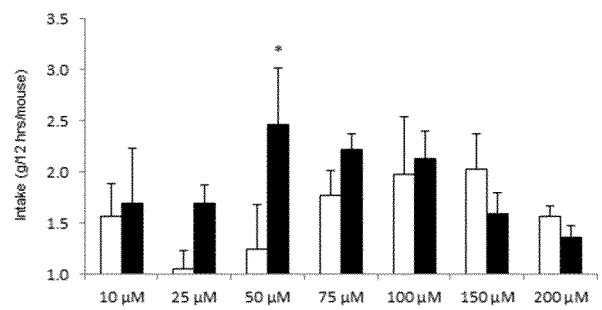
FIG. 6A: shows the dose-dependent effect of NKS-3. n=18 per group.
Figure 7:
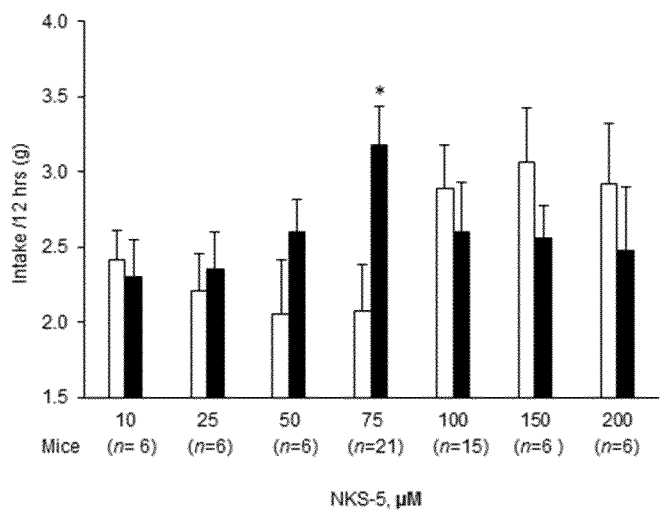
FIG. 7: Gustatory preference for the linoleic acid derivative NKS-5 according to the invention in a two bottle-preference test. Preferential consumption over a period of 12 hours (in g). The n represents the number of mice used in each experimental condition. The asterisk shows the highly significant difference (p<0.001) between the respective control solution and test molecule (NKS-5) according to the student t-test of significance.

Experiment 1 (FIG. 5, FIG. 6A, FIG. 7)

control solutions contain 0.3% xanthan gum, w/v, (Sigma Life Science, USA) in water to reproduce lipid texture and minimize bias due to differences in appearance between the two bottles;

the experimental solution contains, in addition to xanthan gum, 0.3% (w/v), either the "test compound" according to the invention at a concentration varying from 10 to 200 μM (NKS-3, FIG. 6A or NKS-5, FIG. 7) or linoleic acid at 0.2% (v/v) (control test, FIG. 5). To avoid the preference for one side, the position of each bottle is changed during each test.

Figure 6B:
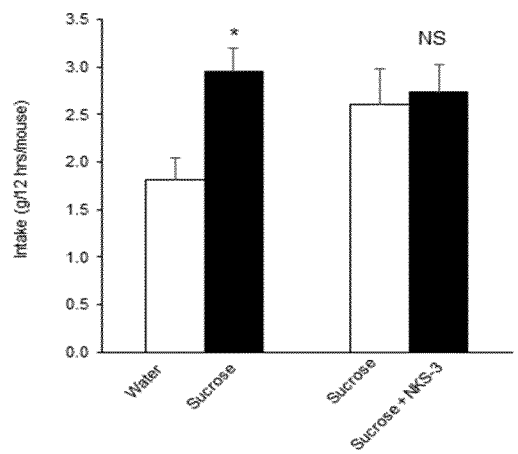
FIG. 6B: shows the preference for a solution-containing sugar (4%, w/v) and NKS-3 plus sugar (4%, w/v). The results are mean±SD. n=6 mice per group. The asterisk shows the significant difference as compared to the control solution (p<0.001) as per statistical students t-test of significance. NS=insignificant differences as compared to the respective control (sucrose) solution.

Experiment 2 (FIG. 6B and FIG. 8): gustatory properties control solutions contain 2% of sucrose (w/v);
the experimental solution contains, in addition to sucrose (2% w/v), the "test compound" according to the invention (NKS-3, FIG. 6B or NKS-5, FIG. 8) at a concentration of 50 μM.

To estimate the consumption of control and experimental solutions, the bottles are weighed before and after each experiment. The mice are allowed to take rest for 48 hours between each experiment.

3.2 Results (FIG. 5 to FIG. 8)

a—NKS-3

As shown in FIG. 5, the mice exhibit a strong preference for the natural fat linoleic acid (LA) as compared to xanthan gum in the two-bottle preference test. As it is similarly shown by FIG. 6A, mice exhibit spontaneous preference for a solution containing the linoleic acid according to the invention, i.e. NKS-3 as compared to the control solution containing xanthan gum. The preference is optimal at a concentration of 50 μM of NKS-3.

In addition, in order to check whether the NKS-3 might increase the gustatory properties of a palatable solution, comparative tests have been performed between a bottle of sucrose and a bottle comprising, in addition to sucrose, NKS-3 (FIG. 6B) (experiment 2 described above). It was observed that the NKS-3 failed to enhance the palatability of a sucrose-containing solution. The mice exhibited a spontaneous preference for a sweet solution as it is an innate taste modality (FIG. 8).

b—NKS-5

Similarly, mice exhibit spontaneous preference for a solution containing NKS-5. It can be observed from FIG. 7 that mice prefer NKS-5 at 75 μM. This is much lesser (93 times) than a fatty acid solution employed for two-bottle preference test.

Figure 8:
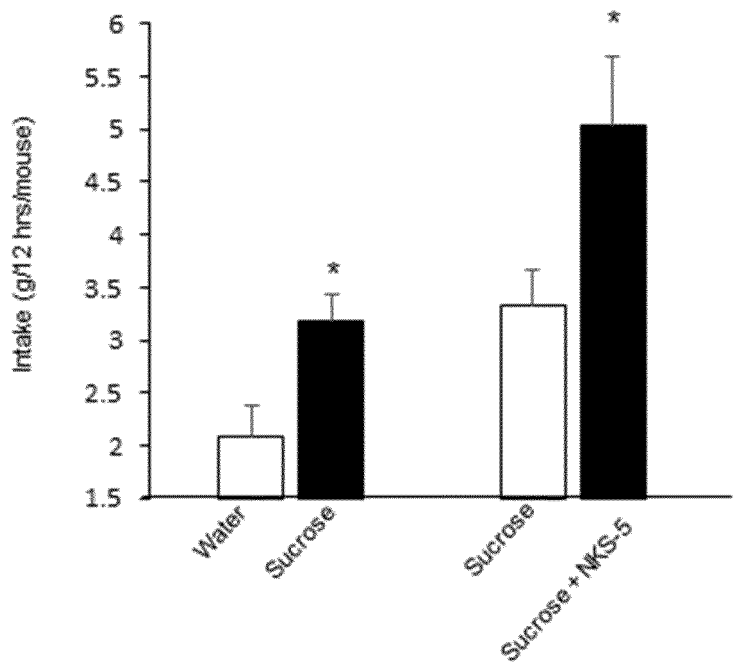
FIG. 8: Effect of NKS-5 according to the invention on sweet preference. The mice were subjected to two bottles, one containing 4% (w/v) sugar (control) and the other one containing a test solution (sugar, 4% and NKS-5). Preferential consumption over a period of 12 hours (in g) was recorded as described here-above. The results are mean±SD. n=6 mice per group. The asterisk shows the highly significant difference (p<0.001) between the control solution and the test molecule (chemical compound) according to the student t-test of significance.

In addition, once dissolved in a palatable solution, the NKS-5 also conserves its gustatory properties (FIG. 8). Alternatively, it can be also alluded that NKS-5 increases the palatability of a sweet solution.

4. Binding Properties

The interactions/binding properties of NKS-3 and NKS-5 with CD36 and GPR120 were studied by simulation.

3.1 Materials and Methods

We used the "Docking" properties by employing Autodock software. The structure box was determined by Autodock grid box, and Autodock Vina was used to calculate the preferred orientation of the analogous molecules towards the protein CD36 and GPR120 to calculate the affinity score of binding of these FAA with CD36 and GPR120.

We used the Docking Discovery Studio to visualize the types of interactions between these molecules and the proteins.

3.2 Results (FIG. 9 to FIG. 12)

a—CD36

Figure 9A:
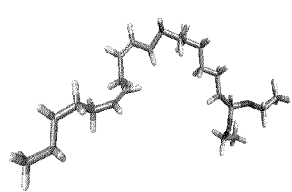
FIG. 9: 3D structure of the linoleic acid derivatives NKS-3 (FIG. 9A) and NKS-5 (FIG. 9B) according to the invention.
Figure 9B:
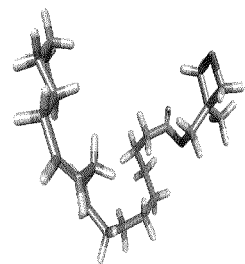

It was observed from FIG. 9A and FIG. 9B that NKS-3 and NKS-5 retain a 3D structure with their free ends for binding with lipid receptors.

Figure 10:
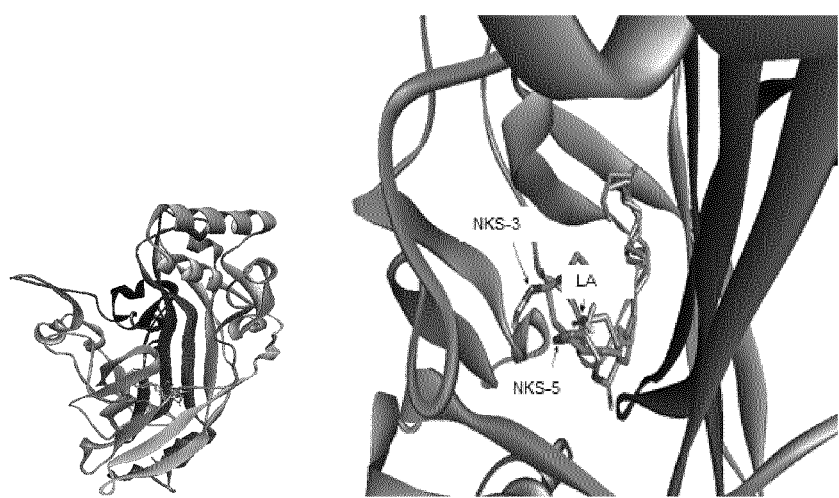
FIG. 10: Interaction of NKS-3, NKS-5 of the invention and Linoleic acid (control) with different amino acids (GLU$^{418}$, LYS$^{385}$, Phe$^{266}$ and Ala$^{251}$) of CD36 inside the 3D pocket of the receptor.

Their kinetic interactions with CD36 have been explored by the Applicant (FIG. 10). It can be seen from this figure that NKS-3 and NKS-5 bound, like linoleic acid, to different amino acid residues with an affinity score of −7.3 to −7.9 Kcal/mol (Table 1 below).

TABLE 1

Affinity score of agonists with the 3D structure of CD36

| Ligands | Target | Affinity score (Kcal/mol) | Amino acids |
|---|---|---|---|
| Linoleic acid | CD36 | −7.3 | $Glu^{418}$, $Ile^{275}$ |
| NKS-3 | CD36 | −7.4 | $Glu^{418}$, $Lys^{385}$, $Phe^{266}$, $Asp^{256}$, $Asp^{206}$ |
| NKS-5 | CD36 | −7.9 | $Glu^{418}$, $Lys^{385}$, $Phe^{266}$, $Ala^{251}$ |

Figure 11:
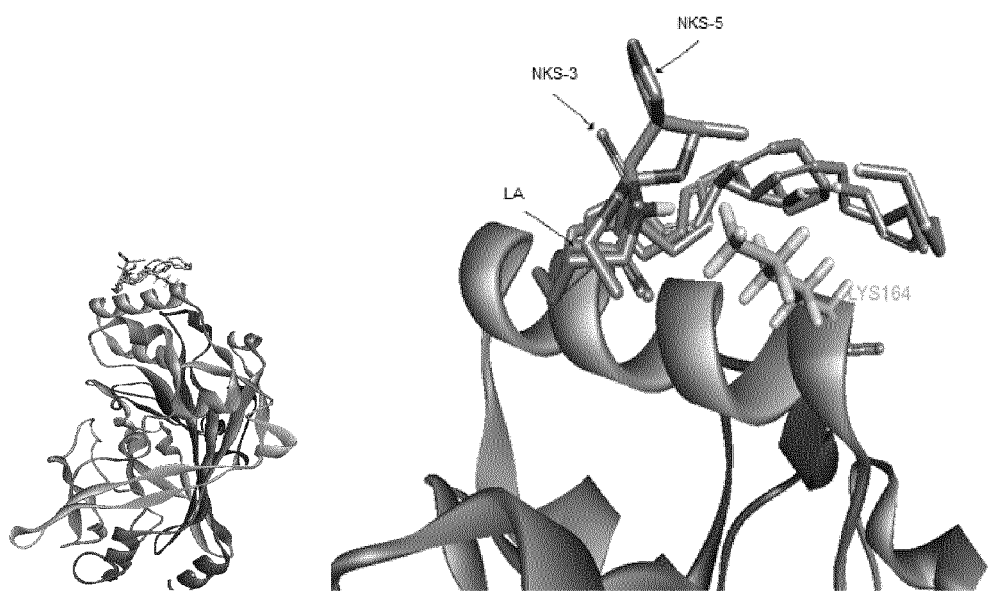
FIG. 11: Interaction of NKS-3, NKS-5 of the invention and Linoleic acid (control) with the LYS$^{164}$ (lysine 164) residue of CD36 within the 3D pocket of the receptor.

Moreover, in the literature, it has been demonstrated that the lead molecule (linoleic acid) binds particularly to the $Lys^{164}$ residue in the CD36 receptor pocket (Kuda O et al, "Sulfo-N-succinimidyl oleate (SSO) inhibits fatty acid uptake and signaling for intracellular calcium via binding CD36 lysine 164: SSO also inhibits oxidized low-density lipoprotein uptake by macrophages". *J. Biol. Chem.* 2013, May 31, 288(22), 15547-55). Thus, this interaction with $Lys^{164}$ of CD36 has also been studied by the Applicant (FIG. 11).

On this figure, it can be observed that the two FAA according to the invention (NKS-3 and NKS-5) behave as linoleic acid with respect to their binding with CD36 $Lys^{164}$. The affinity of this interaction between the three molecules (NKS-3, NKS-5 and LA) is from −3 to −3.2 Kcal/mol (Table 2 below).

TABLE 2

Affinity score of agonists with the 3D structure of CD36 with $Lysine^{164}$.

| Ligand (Kcal/mol) | Target/ $Lys^{164}$ | Affinity score | Amino acids |
|---|---|---|---|
| Linoleic acid | CD36 | −3.2 | $Lys^{164}$ |
| NKS-3 | CD36 | −3.0 | $Lys^{164}$ |
| NKS-5 | CD36 | −2.8 | $Lys^{164}$, $Leu^{161}$ |
| SSO | CD36 | −3.1 | $Lys^{164}$ |

All these observations demonstrate that the two FAA according to the invention have a very important potential in terms of their modulating properties of lingual CD36.

b—GPR120

Figure 12:
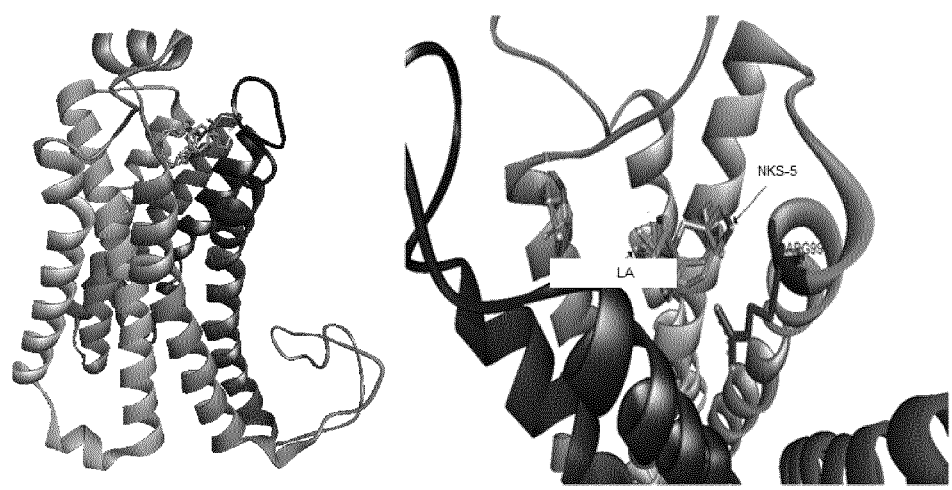
FIG. 12: Interaction of NKS-5 of the invention and Linoleic acid (control) in the 3D structure complex of the GPR120.

As shown by FIG. 12, the FAA according to the invention, especially NKS-5, also bind to GPR120 receptor.

Table 3 below shows the affinity constants between NKS-5, LA and GPR120 receptor. It

TABLE 3

Affinity score of agonists with the 3D structure of the GPR120.

| Ligands (Kcal/mol) | Target | Affinity score | Amino acids |
|---|---|---|---|
| Linoleic acid (LA) | GPR120 | −5.3 | $Arg^{99}$, $Val^{98}$, $Phe^{320}$, $Ser^{317}$ |
| NKS-5 | GPR120 | −5.7 | $Arg^{99}$, $Phe^{320}$, $Val^{98}$, $Phe^{319}$, $Pro^{316}$ |

It can be observed that linoleic acid and NKS-5 possess almost similar affinity for GPR120.

5. Anti-Obesity Effects

5.1 Materials and Methods a—Mice and Diet-Induced Obesity:

C57BL/6J male mice, aged between 6 to 10 weeks (16-20 g), were obtained from Janvier Labs (France). They were housed individually in a controlled environment with a 12 h light/dark cycle with food (SAFE, France) and water ad libitum. The palm oil (Huilerie Vigean, France) was the main fat component in high-fat diets. The high-fat diet was prepared weekly and stored at 4° C. until further use. The study was conducted as per Declaration of Helsinki and European ethical guidelines for the care and use of animals for experimentation. All the experimental protocols (protocol number: 16158) were approved by the Regional Ethical Committee of the University of Burgundy (Dijon, France).

The mice were grouped at random (n=10/group) and fed with either of the following diets: standard diet (STD) or high-fat diet (HFD). The body weight, food, and water intake were measured, weekly.

| Composition of the diets | | |
| --- | --- | --- |
| Content (%) | STD | HFD |
| Proteins | 66.8 | 40.07 |
| starch | 16.10 | 14.6 |
| Fats | 3.10 | 35.3 |
| Cholesterol | 0.03 | |
| Cellulose | 3.9 | 2.7 |
| Vitamins | 5 | 3.4 |
| Minerals | 5.1 | 3.9 |
| Energy (Kcal/100 g) | 359.5 | 536.65 |
| Fat energy (% of total energy) | 8 | 60 |

Standard diet (STD);
high-fat diet (HFD)

| Fatty acid composition of the diets | | |
| --- | --- | --- |
| Fatty acids (%) | STD | HFD |
| SFA | 18.82 | 45.85 |
| MUFA | 26.38 | 40.02 |
| PUFA | 54.8 | 14.13 |

Standard diet (STD);
high-fat diet (HFD)
SFA: saturated fatty acids;
MUFA: monounsaturated fatty acids;
PUFA: polyunsaturated fatty acids.

After 10 weeks of feeding the diets, obese animals were divided into two groups: one groups continued to be fed on the same HFD; however, another group was fed on the same diet and received either NKS-3 or NKS-5) until $28^{th}$ of weeks of experimentation. At the end, the animals were sacrificed, under a fasting condition, and used for different analysis in blood and different tissues.

b—Determination of Biochemical Parameters:

The rat/mouse insulin ELISA kit was obtained from EMD Millipore (USA). ELISA kits for CCK, PYY and GLP-1 were purchased from Cloud-Clone Corp. (USA). The ALAT (Alanine Amino Transferase) was determined by an automatic analyzer (Gilford Model 2000 system, a Beckman System T.R).

c—Liver Histology:

The liver of the mice at the time of sacrifice were fixed in formaldehyde and then dehydrated by passaging into ethanoic media. The liver tissues were embedded into the paraffin and 5μ thick section were cut by the microtome as per standard procedures. The slides, containing tissues, were stained by hematoxylin and eosin dyes as per standard methods. The stained slides were observed under Zeiss light microscope at 10× or 20× magnifications.

d—Statistical Analysis:

Results are expressed as mean±SEM (standard error of mean). Data were analyzed by using Statistica (4.1, Statsoft, Paris, France). The significance of difference between groups was determined by one-way analysis of variance (ANOVA), followed by least-significant-difference (LSD) test. For all the tests, the significance level chosen was $p<0.05$.

Figure 13A:
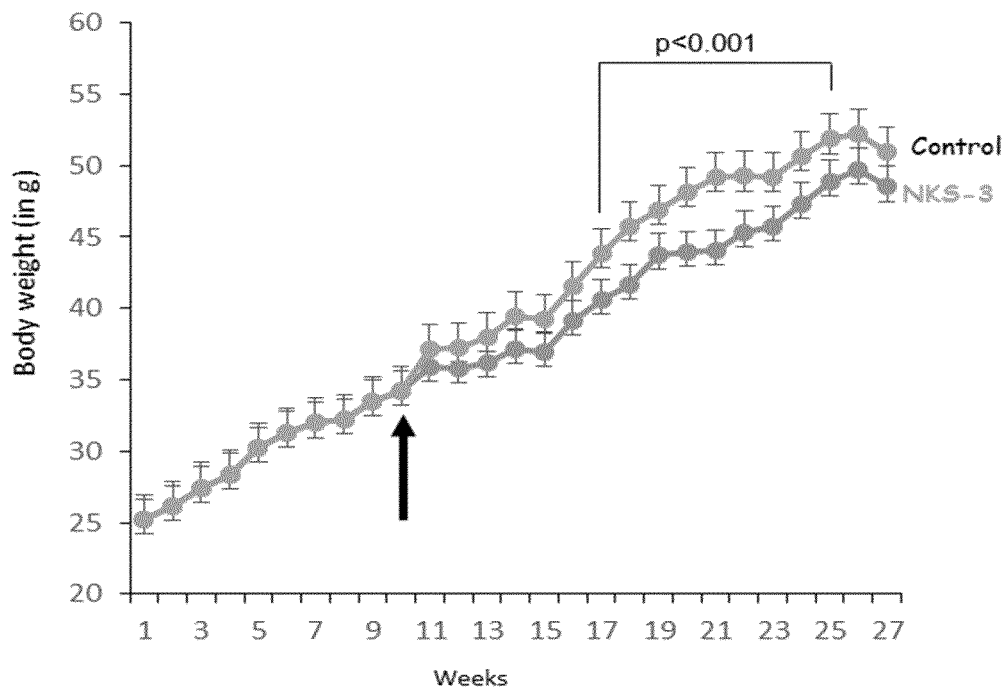
FIG. 13: Effect of NKS-3 (FIG. 13A) and NKS-5 (FIG. 13B) on diet-induced obesity. The animals were fed a high-fat diet (HFD) for 28 weeks; however, from 10th week onwards, the baby-bottles/feeders contained either control solution (control group) or analogues (NKS-3 or NKS-5). The arrows indicate when the lipid analogues were added. The results are expressed as the means±SEM (n=10). p values represent the significant differences between the group of mice given either water and analogues in the feeder bottles.
Figure 13B:
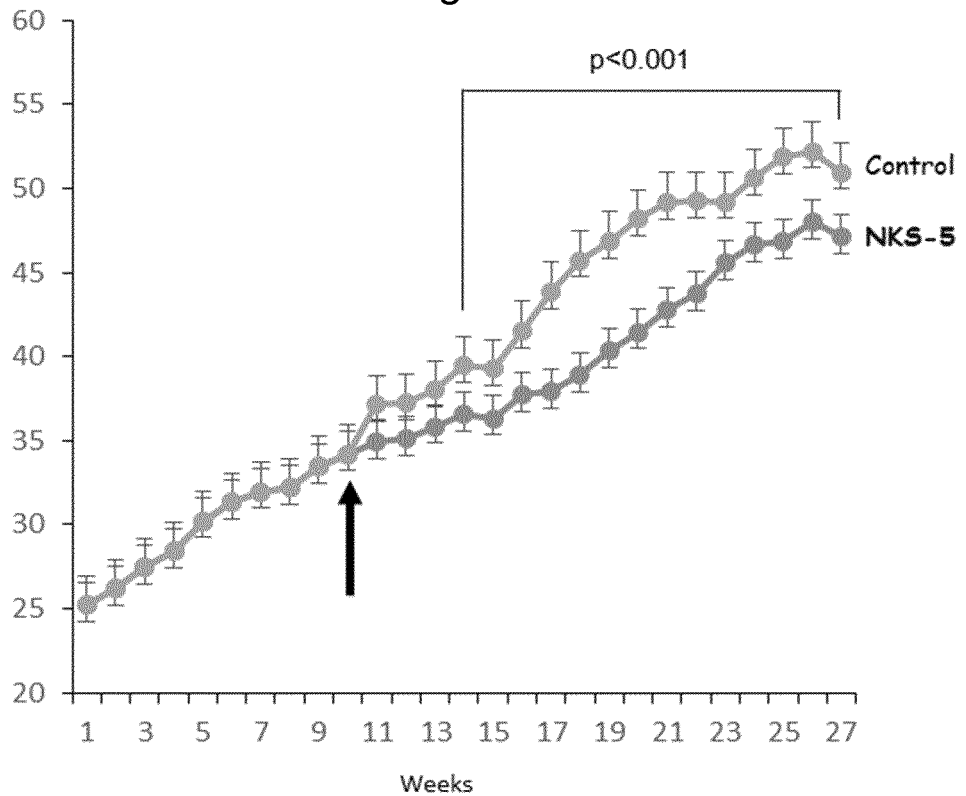

5.2 Fat Taste Analogues According to the Invention Exert Anti-Obesity Effects in Mice In order to elucidate the beneficial effects and especially during obesity, experiments were conducted on obese C57BL/6J mice. The mice were maintained on a high-fat diet for 10 weeks and an increase in body weight in a progressive and linear manner was observed in these animals. In order to test the curative/interventional effects on obesity, the animals were divided into two groups: one group that consume only the high-fat diet (HFD) and the other consuming the same diet and also receiving NKS-3 or NKS-5 in adlibitum baby bottles/feeders. From the $10^{th}$ week of the diet, lipid analogues were introduced into the bottles at concentrations that corresponded to their preference in the double choice test (NKS-5 at 75 μM; NKS-3 at 50 μM). From the first week of administration of analogues, there was a significant decrease in body weight in the obese mouse by these two lipid analogues (NKS-5 was more powerful than NKS-3). In addition, the decrease in obesity was maintained until the $28^{th}$ week of feeding a HFD (FIGS. 13A and 13B). It should be noted that these lipid analogues exerted no effect on the body weight of the control animals, receiving the normal diet, suggesting that the lipid analogues act only in the case of a pathology.

The study was stopped after the $28^{th}$ week of the diet because the animals reached the age of 34 weeks and beyond that age, the aging factor may interfere with the growth.

5.3 Lipid Analogues Reduce Obesity by Releasing Anorectic Peptides/Hormones

Figure 14:
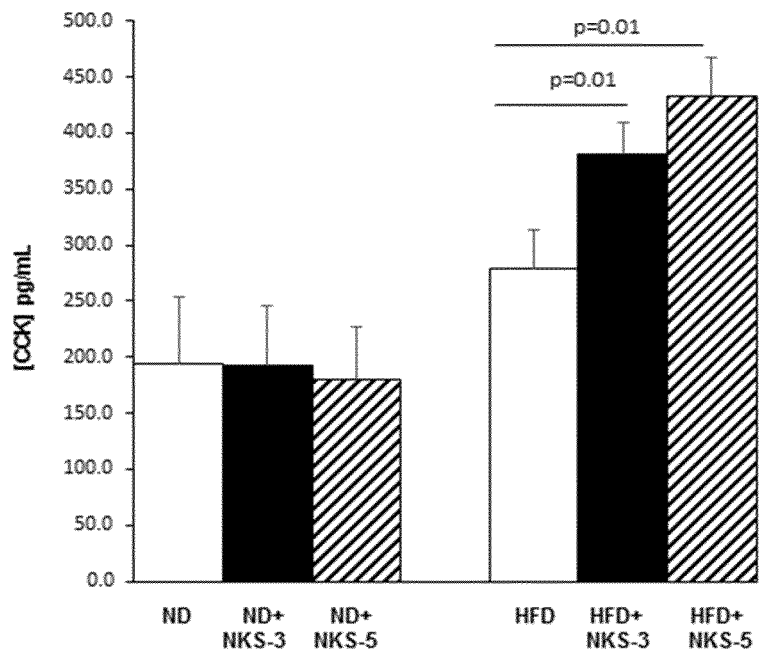
FIG. 14: CCK concentrations in the peripheral circulation. The results are expressed as the means±SEM (n=10). p values represent the significant differences between the group of mice given either water and analogues in the feeder bottles. Abbreviations: ND=normal or standard diet; HFD=high-fat diet.
Figure 15:
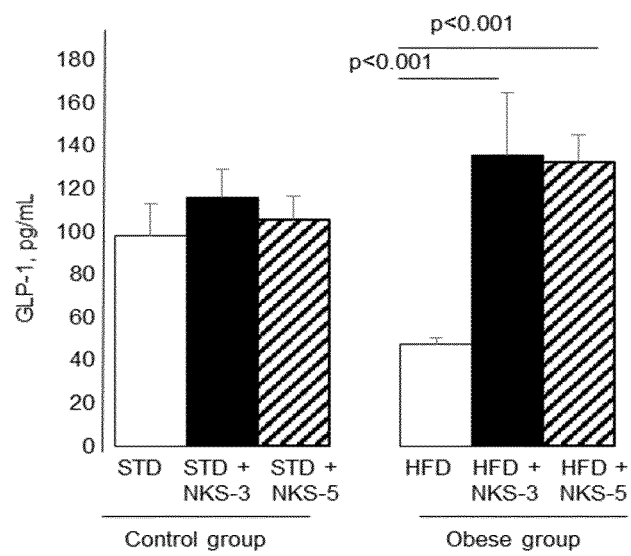
FIG. 15: GLP-1 concentrations in the peripheral blood circulation. The results are expressed as the means±SEM (n=10). p values represent the significant differences between the group of mice given either water and analogues in the feeder bottles. Abbreviations: ND=normal or standard diet; HFD=high-fat diet.
Figure 16:
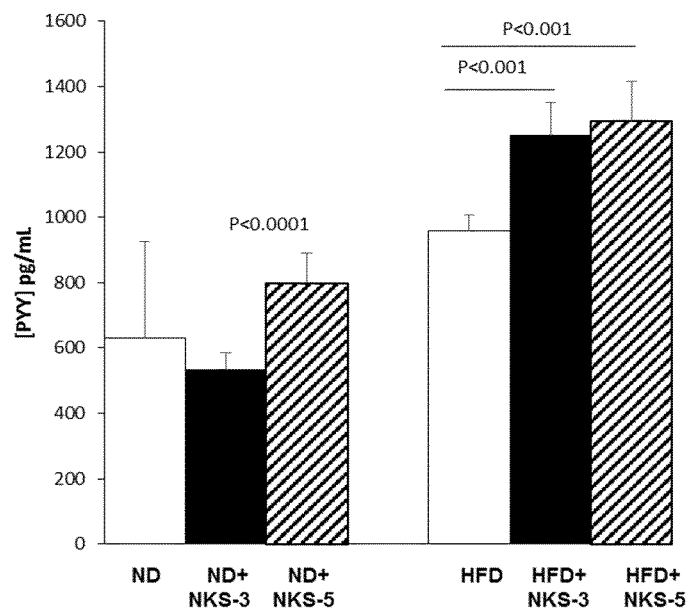
FIG. 16: PYY concentrations in the peripheral blood circulation. The results are expressed as the means±SEM (n=10). p values represent the significant differences between the group of mice given either water and analogues in the feeder bottles.

The blood/sera concentrations of various factors/hormones/peptides released by the gastrointestinal tract were quantified. The secretion of cholecystokinin (CCK) by the pancreas is considered to be one of the most anorexigen factors that plays a role in satiety, exerting its action on the vagus nerve (nerve X) that conveys the message from the duodenum/intestine to the central nervous system to stop food intake. Some agents that increase the secretion of CCK very significantly can trigger satiety and decrease food intake. Other peptides such as glucagon-like petide-1 (GLP-1), released by enterochromaffin cells of the intestine (jejunum) and a peptide of the NPY family, called PYY, released by the stomach, also exert strong satiety effects in the late phase of food intake. Lipid analogues according to the invention were observed to trigger high release of CCK (FIG. 14), GLP-1 (FIG. 15) and PYY (FIG. 16) in the blood circulation of animals in the obese group, receiving fat taste analogues.

These observations suggest that the anti-obesity effects of lipid analogues of the invention are exerted via their action on the release of anorectic/satiety agents that may decrease the food intake.

5.4 Fat Taste Analogues Decrease the Pro-Inflammatory Status in Obese Animals It is now well established that obesity is associated with low-grade inflammation, characterized by the increase of pro-inflammatory factors in the peripheral blood. These factors are, principally, as follows: interleukin-1 (IL-1), inetroleukin-6 (IL-6) and tumor necrosis factor-alpha (TNF-alpha). These factors are released mainly by adipocytes that differentiate into macrophage-like cells during obesity.

Figure 17:
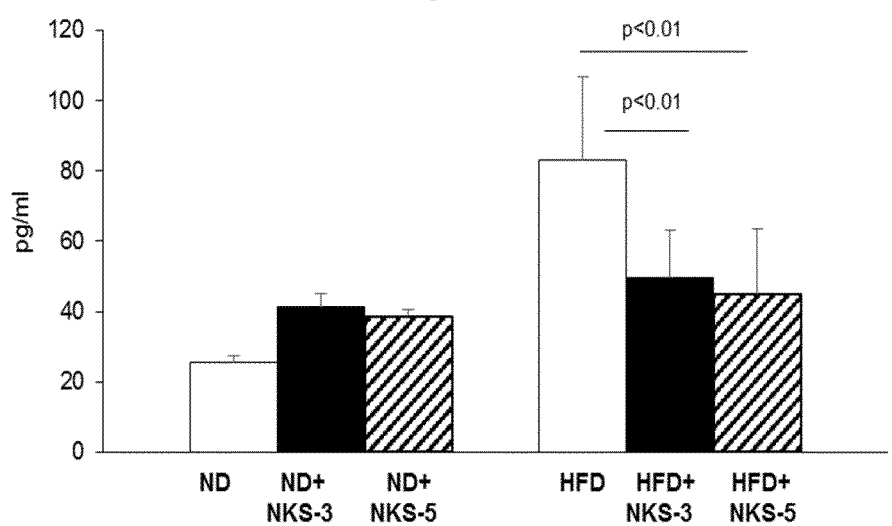
FIG. 17: IL-6 concentrations in the peripheral blood circulation. The results are expressed as the means±SEM (n=10). p values represent the significant differences between the group of mice given either water and analogues in the feeder bottles.

NKS-3 and NKS-4 lipid analogues according to the invention were observed to decrease the circulating concentrations of IL-6 (FIG. 17) and other mediators of inflammation in obese animals, who received both NKS-3 and NKS-5 in the bottle/feeders.

5.5 Fat Taste Analogues Decrease Insulinemia in Obese Animals

Insulin is a polypeptide hormone synthetized by the β-cells of islets of Langerhans in the pancreas. Its role is to maintain the level of sugar present in the blood at a stable level. When blood sugar levels increase a little because of the consumption of high-sugar products, insulin is responsible for transporting this excess sugar to the cells of the muscles, the liver and also adipose tissue.

Figure 18:
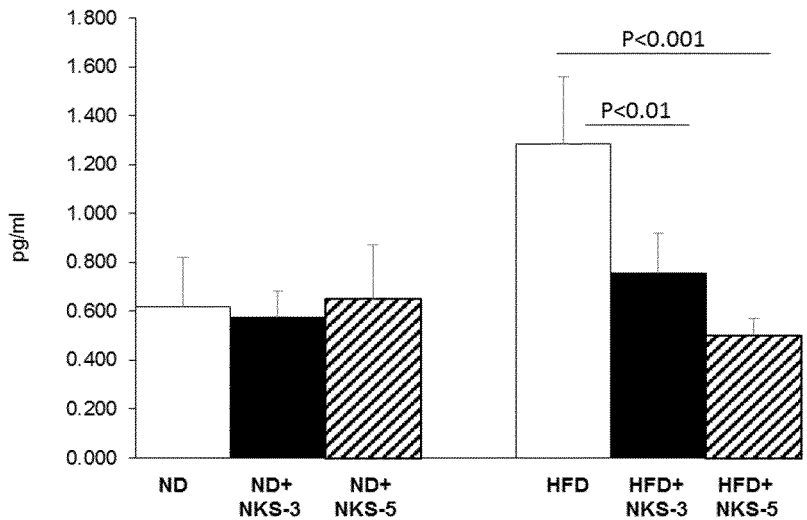
FIG. 18: Insulin concentrations in the peripheral blood circulation. The results are expressed as the means±SEM (n=10). p values represent the significant differences between the group of mice given either water and analogues in the feeder bottles.

The obese subjects suffer from pre-diabetic state that is marked by high concentrations of blood glucose. This state is called insulin-resistance as this hormone is not able to control blood glucose. In our study, we observed that obese animals were marked by insulin levels and addition of NKS-3 or NKS-5 decreases the insulin concentrations (FIG. 18).

5.6 Lipid Analogues Protect Liver Function

The liver is the mainly involved in lipid metabolism and elimination of toxic substances. In case of obesity (or high alcohol consumption), we observe a liver steatosis.

Figure 19:
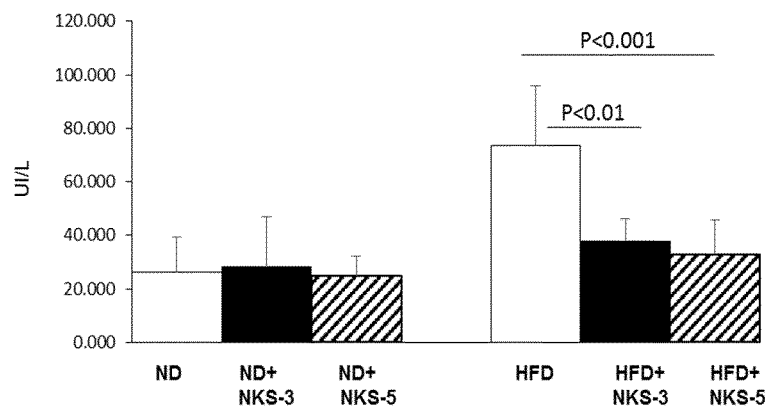
FIG. 19: ALAT concentrations in the peripheral blood circulation. The results are expressed as the means±SEM (n=10). p values represent the significant differences between the group of mice given either water and analogues in the feeder bottles.

The ALAT (Alanine Amino Transferase, also called Pyruvic Glutamic Transaminase), is a detoxifying enzyme, present mainly in striated muscles, voluntary muscles, and especially in the liver. Its dosage is very useful for the diagnosis of certain diseases, in particular muscular and hepatic diseases. Thus, in case of destruction of the liver cells as in hepatitis or cirrhosis, the level of ALT in the blood is increased. The blood concentrations of ALAT was observed to increase significantly in the blood of obese animals compared to normal mice, and the fat taste analogues NKS-3 and NKS-5 according to the invention decreased its concentration in obese animals (FIG. 19).

Figure 20:
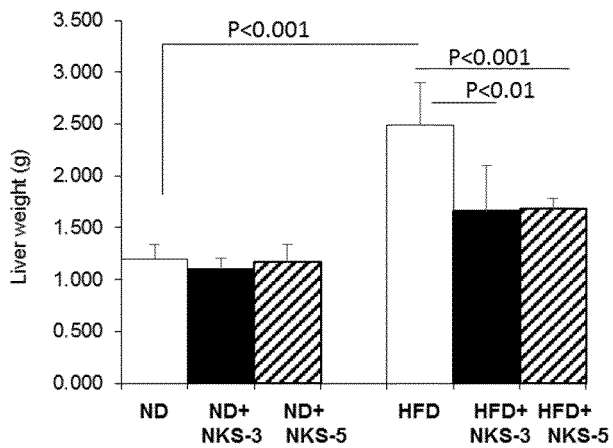
FIG. 20: Liver weight in normal diet fed and HFD-fed animals. The results are expressed as the means±SEM (n=10). p values represent the significant differences between the group of mice given either water and analogues in the feeder bottles.

It is also noteworthy that weight of the liver that was increased in obese mice was significantly curtailed only in obese animals (FIG. 20).

Figure 21:
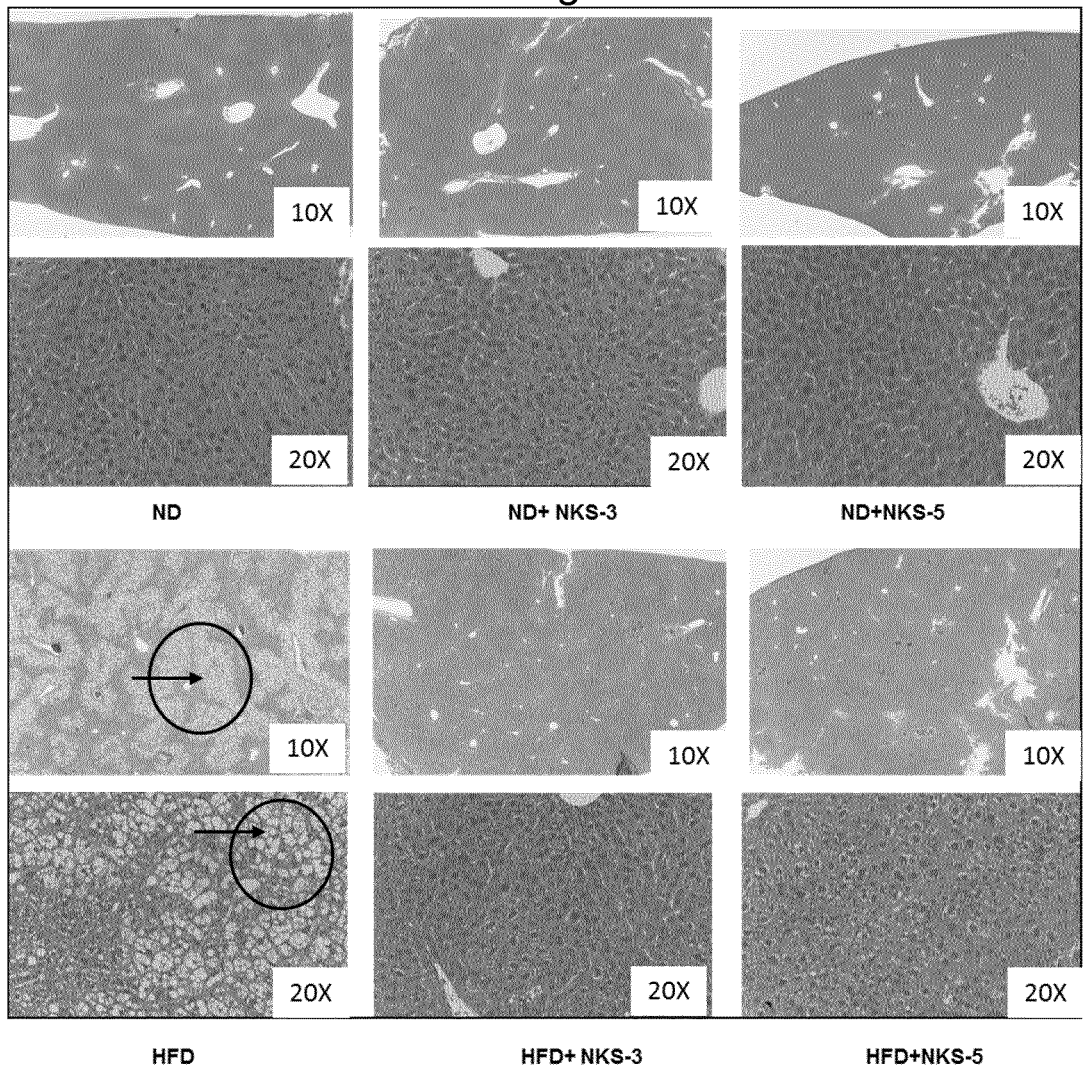
FIG. 21: Liver histological examination of mice fed either normal diet or a HFD. The histological examinations were performed after the sacrifice of the animals. The liver tissues were embedded in the paraffin sections and 5-micron thick sections were cut by microtomes and the slides were stained in hematoxylin and eosin and the slides were observed under a light microscope. The circles with arrow show the liver steatosis in obese mice, fed a HFD only.

The liver of obese subjects suffers from metabolic steatohepatitis or NASH (non-alcoholic steatosis hepatitis) syndrome. The prevalence of NASH syndrome and severe steatosis (fibrosis/cirrhosis) is correlated with the degree of obesity. The histological changes in the liver were also studied. Very beneficial effects of fat taste analogues were surprisingly observed. It is to note that the analogues (NKS-3 and NKS-5) did not exert any effect in normal diet fed mice (FIG. 21). However, the liver of obese mice was affected with steatosis and the lipid analogues exerted curative effects in liver sections (FIG. 21).

The invention claimed is:

1. Linoleic acid derivative of Formula (I) below comprising a hydrophobic part $C_{17}H_{31}$ linked to a polar head part "A":

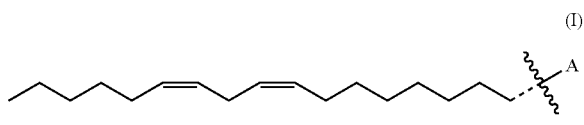

(I)

wherein said polar head part A is selected from $A^1$ to $A^4$ below:

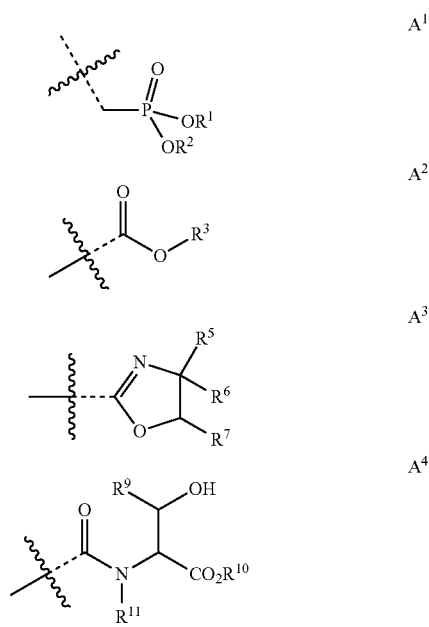

wherein
$R^1$ and $R^2$ are independently selected from the group composed of H or a saturated or unsaturated, straight or branched alkyl group containing 1 to 8 carbon atoms, or $R^1$ and $R^2$ are linked together to form a divalent radical of formula $—R^1\text{-}R^2$;
$R^3$ is independently selected from the group composed of:

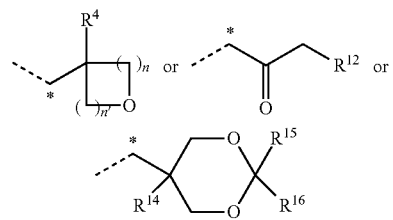

wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1, provided that $R^4$ is different from H when n=4 and n'=0 or when n=1 and n'=0,"*" is the carbon atom which is attached to the oxygen atom of the $A^2$ polar head;

$R^{12}$ is selected from H or a saturated or unsaturated, straight or branched alkyl group containing 1 to 4 carbon atoms, or an aromatic group or —$CO_2R^{13}$ in which $R^{13}$ is a saturated alkyl group containing 1 to 4 carbon atoms, and $R^{14}$, $R^{15}$, $R^{16}$ is independently selected from H or $CH_3$;

$R^5$, $R^6$ and $R^7$ are independently selected from the group composed of H or a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms; with the proviso that when $R^7$=H or $CH_3$, $R^5$ and $R^6$ are different from each other;

$R^9$ to $R^{11}$ are independently selected from the group composed of H or a saturated or unsaturated, straight or branched alkyl group containing 1 to 4 carbon atoms, provided that when $R^9$ and $R^{11}$=H, $R^{10}$ is different from an ethyl-group or H;

or a pharmaceutically/food quality acceptable salt thereof.

2. The linoleic acid derivative according to claim 1, having a molecular weight ranging from about 300 to about 600 g/mol.

3. The linoleic acid derivative according to claim 1, wherein in $A^1$, $R^1$ and $R^2$ are a saturated or unsaturated, straight or branched alkyl group containing 1 to 2 carbon atoms, or a pharmaceutically/food quality acceptable salt thereof.

4. The linoleic acid derivative according to claim 1, wherein in $A^2$, $R^3$ is

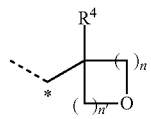

wherein $R^4$ is $CH_3$, when n=1, and n'=0, or n=1 and n'=1, or still n=4 and n'=0, or a pharmaceutically/food quality acceptable salt thereof.

5. The linoleic acid derivative according to claim 1, wherein in $A^2$, $R^3$ is

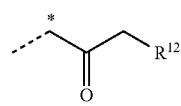

wherein $R^{12}$ is H, or a pharmaceutically/food quality acceptable salt thereof.

6. The linoleic acid derivative according to claim 1, wherein in $A^2$, $R^3$ is

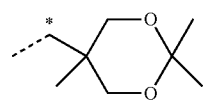

or a pharmaceutically/food quality acceptable salt thereof.

7. The linoleic acid derivative according to claim 1, wherein in $A^3$, $R^5$ is H, $R^6$ is —$CO_2CH_3$ and $R^7$ is H, or a pharmaceutically/food quality acceptable salt thereof.

8. The linoleic acid derivative according to claim 1, wherein in $A^4$, $R^9$ is H, $R^{10}$ is $CH_3$, and $R^{11}$ is H, or a pharmaceutically/food quality acceptable salt thereof.

9. A medicament comprising:
a linoleic acid derivative of Formula (I) below comprising a hydrophobic part $C_{17}H_{31}$ linked to a polar head part "A":

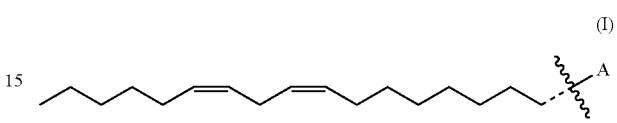

wherein said polar head part A is selected from $A^1$ to $A^4$ below:

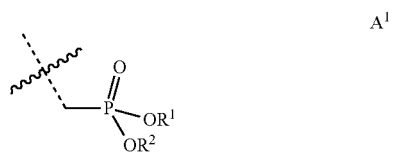

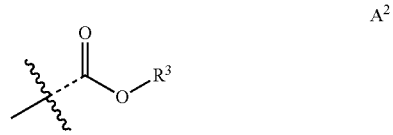

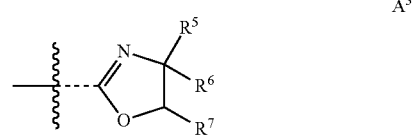

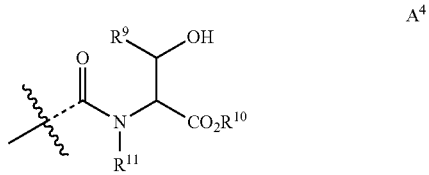

wherein
$R^1$ and $R^2$ are independently selected from the group composed of H or a saturated or unsaturated, straight or branched alkyl group containing 1 to 8 carbon atoms, or $R^1$ and $R^2$ are linked together to form a divalent radical of formula —$R^1$—$R^2$—;

$R^3$ is independently selected from the group composed of:

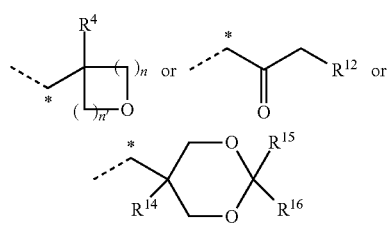

wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1; provided that $R^4$ is different from H when n=4 and n'=0 or when n=1 and n'=0, "*" is the carbon atom which is attached to the oxygen atom of the $A^2$ polar head;

$R^{12}$ is selected from H or a saturated or unsaturated, straight or branched alkyl group containing 1 to 4 carbon atoms, or an aromatic group or —$CO_2R^{13}$ in which $R^{13}$ is a saturated alkyl group containing 1 to 4 carbon atoms, and $R^{14}$, $R^{15}$, $R^{16}$ is independently selected from H or $CH_3$;

$R^5$, $R^6$ and $R^7$ are independently selected from the group composed of H or a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms; with the proviso that when R7=H or CH3, R5 and R6 are different from each other;

$R^9$ to $R^{11}$ are independently selected from the group composed of H or a saturated or unsaturated, straight or branched alkyl group containing 1 to 4 carbon atoms, provided that when $R^9$ and $R^{11}$=H, $R^{10}$ is different from an ethyl-group or H;

or a pharmaceutically/food quality acceptable salt thereof.

10. A pharmaceutical composition or food composition comprising, respectively,
at least one pharmaceutically acceptable carrier and at least one linoleic acid derivative according to claim 9, or
at least one food ingredient and/or at least one food additive and at least one linoleic acid derivative according to claim 9.

11. A method for treatment of a disorder modulated by the GPR120 receptor and/or the CD36 receptor, comprising administering to a subject in need thereof a therapeutically effective amount of said linoleic acid derivative of claim 1, wherein the disorder modulated by the GPR120 receptor and/or the CD36 receptor is selected from the group consisting of: diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, body weight disorder, fatty liver disease, dyslipidemia, hyperlipidemia, hypertriglyceridemia, hypercholesterolemia, low high-density lipoprotein (HDL), high low-density lipoprotein (LDL), lipid disorders and liver diseases.

12. An appetite suppressant comprising the linoleic acid derivative according to claim 1.

13. A food supplement or dietary supplement for animal or human food, or ready-cooked dish, or animal feedstuff, comprising the food composition of claim 10.

14. A method for enhancing taste, modulating taste, suppressing appetite, or improving the physical appearance of individuals, comprising applying an effective amount of the linoleic acid derivative according to claim 1.

15. The linoleic acid derivative of claim 1, wherein:
$R^1$—$R^2$— is —$CH_2$—$CH_2$— or —$(CH_2)_3$—;
$R^{14}$=$R^{15}$=$R^{16}$=$CH_3$ or $R^{14}$=H or $CH_3$ and $R^{15}$=$R^{16}$=H; and
$R^5$ and $R^6$ are different from each other when they correspond to $CH_3$ or to H.

16. The linoleic acid derivative according to claim 1, wherein in $A^1$, $R^1$ and $R^2$ are a saturated or unsaturated, straight or branched alkyl group containing 1 to 2 carbon atoms, or a pharmaceutically/food quality acceptable salt thereof, and $R^1$ and $R^2$ are ethyl group.

17. The linoleic acid derivative of claim 9, wherein:
—$R^1$—$R^2$— is —$CH_2$—$CH_2$— or —$(CH_2)_3$—;
$R^4$ is different from H when n=4 and n'=0 or when n=1 and n'=0;
$R^{14}$=$R^{15}$=$R^{16}$=$CH_3$ or $R^{14}$=H or $CH_3$ and $R^{15}$=$R^{16}$=H;
when $R^7$=H or $CH_3$, $R^5$ and $R^6$ are different from each other, when they correspond to $CH_3$ or to H; and
when $R^{10}$ and $R^{11}$=H, $R^9$ is different from an ethyl-group or H.

18. The linoleic acid derivative according to claim 2, wherein in $A^1$, $R^1$ and $R^2$ are a saturated or unsaturated, straight or branched alkyl group containing 1 to 2 carbon atoms, or a pharmaceutically/food quality acceptable salt thereof.

19. A method for treatment of a disorder modulated by the GPR120 receptor and/or the CD36 receptor, comprising:
administering to a subject in need thereof a therapeutically effective amount of a pharmaceutically/food quality acceptable salts thereof or pharmaceutical composition according to claim 10, wherein the disorder modulated by the GPR120 receptor and/or the CD36 receptor is selected from the group consisting of: diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, body weight disorder, fatty liver disease, dyslipidemia, hyperlipidemia, hypertriglyceridemia, hypercholesterolemia, low high-density lipoprotein (HDL), high low-density lipoprotein (LDL), lipid disorders and liver diseases.

* * * * *